(12) United States Patent
Corey et al.

(10) Patent No.: US 7,465,720 B2
(45) Date of Patent: Dec. 16, 2008

(54) PROTEASOME INHIBITING β-LACTAM COMPOUNDS

(75) Inventors: Elias J. Corey, Cambridge, MA (US); Philip C. Hogan, St. John's (CA)

(73) Assignee: President and Fellows of Harvard College, Cambridge, MA (US)

( * ) Notice: Subject to any disclaimer, the term of this patent is extended or adjusted under 35 U.S.C. 154(b) by 366 days.

(21) Appl. No.: 11/224,589

(22) Filed: Sep. 12, 2005

(65) Prior Publication Data

US 2007/0060561 A1 Mar. 15, 2007

(51) Int. Cl.
*C07D 487/04* (2006.01)
*A61K 31/407* (2006.01)
*C07D 487/10* (2006.01)
*C07D 405/04* (2006.01)
*C07D 263/26* (2006.01)
*C07F 7/10* (2006.01)

(52) U.S. Cl. ............... 514/210.05; 540/203; 540/200; 548/230

(58) Field of Classification Search ............. 540/203; 514/210.05
See application file for complete search history.

(56) References Cited

U.S. PATENT DOCUMENTS

| | | | |
|---|---|---|---|
| 5,756,764 A | 5/1998 | Fenteany et al. | |
| 5,869,675 A | 2/1999 | Omura et al. | |
| 6,133,308 A | 10/2000 | Soucy et al. | |
| 6,147,223 A | 11/2000 | Fenteany et al. | |
| 6,214,862 B1 | 4/2001 | Fenteany et al. | |
| 6,294,560 B1 | 9/2001 | Soucy et al. | |
| 6,335,358 B1 | 1/2002 | Fenteany et al. | |
| 6,458,825 B1 | 10/2002 | Fenteany et al. | |
| 6,566,553 B2 | 5/2003 | Soucy et al. | |
| 6,645,999 B1 | 11/2003 | Schreiber et al. | |
| 2003/0157695 A1 | 8/2003 | Fenical et al. | |
| 2004/0138196 A1 | 7/2004 | Fenical et al. | |
| 2005/0203162 A1 | 9/2005 | Xiao et al. | |

FOREIGN PATENT DOCUMENTS

| | | |
|---|---|---|
| WO | WO 96/32105 | 10/1996 |
| WO | WO 02/094311 | 11/2002 |
| WO | WO 2004/071382 | 8/2004 |
| WO | WO 2005/002572 A2 | 1/2005 |

OTHER PUBLICATIONS

Hogan, Philip et al., Journal of the American Chemical Society (2005), 127(44), 15386-15387.*
Ritonovir <http://aidsinfo.nih.gov/DrugsNew/DrugDetailNT.aspx?MenuItem=Drugs&Search=On&int_id=244> downloaded from the internet Nov. 23, 2007.*
Norvir (ritonavir) <http://www.hivandhepatitis.com/hiv_and_aids/norvir_effects.html> downloaded from the internet Nov. 23, 2007.*
Yeh et al, J Neurochem. Aug. 2005;94(4):943-56.*
Rockwell et al., Archives of Biochemistry and Biophysics vol. 374, Issue 2, Feb. 15, 2000, pp. 325-333.*
Tabuchi Alzheimer's and Dementia vol. 2, Issue 3, Supplement 1, Jul. 2006, p. S628.*
Ding et al., The FASEB Journal. 2006;20:1055-1063.*
Momose et al., Heterocycles 1999, vol. 51, No. 6, pp. 1321-1343.*
Manchand, J. Org. Chem. 1992, 57, 3473-3478.*
Goldberg et al., Nature Medicine, vol. 8, No. 4, 338-340 (2002).
Feeling, R.H.; Buchanan, G.O.; Mincer, T.J.; Kauffman, C.A.; Jensen, P.R.; Fenical, W., Angew. Chem. Int. Ed., Salinosporamide A: A highly Cytotoxic Proteasome Inhibitor from a Novel Microbial Source, a Marine Bacterium of the New Genus *Salinospora*, 2003, 42, 355-357.
Corey, E.J.; Li, Wei-Dong., Z. Total Synthesis and Biological Activity of Lactacystin, Omuralide and Analogs, Chem. Pharm. Bull., 1999, 47, 1-10.
Corey, E.J., Reichard, G.A.; Kania, R., Studies on the Total Synthesis of Lactacysin. An improved Aldol Coupling reaction and a β-Lactone Intermediate in Thiol Ester Formation, Tetrahedron Lett., 1993, vol. 34, No. 44, 6977-6980.

(Continued)

*Primary Examiner*—Mark L Berch

(57) ABSTRACT

Disclosed is a total synthesis of a biologically active β-Lactam—Compound 3, which is related to Salinosporamide A and Omuralide, both structurally and by its activity as a proteasome inhibitor.

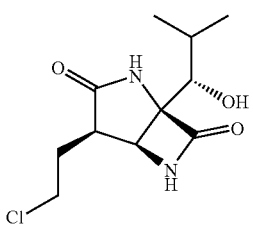

Also disclosed are proteasome inhibiting compounds having the formula:

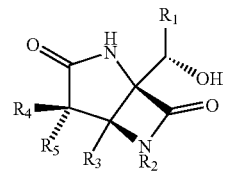

wherein:
$R_1$ is a cyclolower alkyl group; or $R_1$ is a lower alkyl group; and $R_2$ is either hydrogen or a lower alkyl group; $R_3$ is either hydrogen or a lower alkyl group; $R_4$ a halo-lower alkyl group; and $R_5$ is either hydrogen or a lower alkyl group.

15 Claims, 3 Drawing Sheets

OTHER PUBLICATIONS

Corey, E. J.; Reichard, G. A., Total Synthesis of Lactacysin, J. Am. Chem. Soc., 1992, 114, 10677-10678.

Fenteany, G.; Standaert, R.F.; Reichard, G. A.; Corey, E. J.; Schreiber, S. L., A β-lactone related to lactacystin induces neurite outgrowth in a neuroblastoma cell line and inhibits cell cycle progression in an osteosarcoma cell line. Proc. Natl. Acad. Sci. USA, 1994, 91, 3358-3362.

Omura, S., Fujimoto, T., Otoguro, K., Matsuzaki, K., Moriguchi, R., Tanaka, H., Sasaki, Y., Lactacystin, A novel Microbial Metabolite, induces Neuritogenesis of Neuroblastoma Cells, A., J. Antibiot., 1991, 44, 113-116.

Omura, S., Matsuzaki, K., Fujimoto, T., Kosuge, K., Furuya, T., Fujita, S., Nakagawa, Structure of Lactacystin, a new microbial metabolite which induces differentiation of Neuroblastoma Cells, A., J. Antibiot., 1991, 44, 117-118.

Mincer, Tracy, J., Jensen, Paul, R., Kauffman, Christopher, A., and Fenical William, Widespread and Persistent Populations of a Major new Marine Actinomycete Taxon in Ocean Sediments, Appl. Environ. Microbiol., 68, 5005 (2002).

Wilson, Elizabeth, K., Plumbing the Ocean Depths for Drugs, Chemical & Engineering News, vol. 81, No. 3, pp. 37-38 (2003).

Frank, S. A.; Mergott, D. J., Roush, W. R., The Vinylogous Intramolecular Morita—Baylis—Hillman Reaction: Synthesis of Functianalized Cyclopentenes and Cyclohexenes with Trialkylphosphines as Nucleophilic Catalysts, J. Am. Chem. Soc., 2002, 124, 2404-2405.

Mergott, D.J., Frank, S. A., Roush, W. R., Application of the Intramolecular Vinylogous Morita-Baylis-Hillman Reaction toward the Synthesis of the Spinosyn A Tricyclic Nucleus, Org. Lett., 2002, vol. 4, No. 18, 3157-3160.

Aggarwal, V. K., Emme, I., Fulford, S. Y., Correlation between $pK_a$ and Reactivity of Quinuclidine-Based Catalysts in the Baylis-Hillman Reaction: Discovery of Quinuclidine as Optimum Catalyst Leading to Substantial Enhancement of Scope, J. Org. Chem., 2003, 68, 692-700.

Yeo, J. E., Yang, X., Kim, H.J., Koo, S., The intramolecular Baylis-Hillman reaction: easy preparation of versatile substrates, facile reactions, and synthetic applications, J. Chem. Soc., Chem. Commun., 2004, 236-237.

Bols, M., Skrydstrup, T., Silicon-Tethered Reactions, Chem. Rev., 1995, 95, 1253-1277.

Fleming, I., Barbero, A., Walter, D., Sterechemical Control in Organic Synthesis Using Silicon-Containing Compounds, Chem. Rev., 1997, 97, 2063-2092.

Stork, G., Mook, R., Biller, S.A., Rychnovsky, S. D., Free-Radical Cyclization of Bromoacetals. Use in the Construction of Bicyclic Acetals and Lactones. J. Am. Chem. Soc., 1983, 105, 3741-3742.

Stork, G., Sher, P. M., Chen, H.L., Radical Cyclization-Trapping in the Synthesis of Natural Products. A Simple, Stereocontrolled Route to Prostaglandin $F_{2\alpha}$. J. Am. Chem. Soc., 1986, 108, 6384-6385.

Miyake, H., Yamamura, K., Pd(0) Catlyzed Hydrostannation of Conjugated Dienes. A Facile and Highly Regio- and Stereoselective Synthesis of (Z)-2-Alkenylstannanes. Chem. Lett., 1992, 507-508.

Jones, G. R., Landais, Y., The Oxidation of the Carbon-Silicon Bond, Tetrahedron, 1996, 52, 7599-7662.

Corey, E. J., Li, W., Nagamitsu, T., An Efficient and Concise Enantioselective Total Synthesis of lactacystin, Angew. Chem. Int, Ed., 1998, 37, 1676-1679.

Corey, E.J., and Wei-Dong, Z., Total Synthesis and Biological Activity of Lactacystin, Omuralide and Analogs, Chem. Pharm. Bull., 1999, 47, 1-10.

Corey, E., and Wei-Dong, Z., "An Efficient Total Synthesis of a New and Highly Active Analog of Lactacystin," Tetrahedron Letters, vol. 39(41), pp. 7475-7478 (Oct. 1998).

Panek, J., and Masse, C., "Total Synthesis of (+)-Lactacystin," Agnew. Chem. Int. Ed., vol. 38(8) (Apr. 1999), 1093-1094.

Soucy, F., et al., "A Novel and Efficient Synthesis of a Highly Active Analogue of clasto-Lactacystin Beta-Lactone," vol. 121 (43), pp. 9967-9976 (Nov. 1999).

Crane, S., and Corey, E., "A Novel Enantioselective Synthetic Route to Omuralide Analogues with the Potential for Species Selectivity in Proteasome Inhibition," vol. 3(9), pp. 1395-1397 (2001).

Saravanan, P., and Corey, E., "A Short, Stereocontolled, and Practical Synthesis of Alpha-Methylomuralide, a Potent Inhibitor of Proteasome Function," J. Org. Chem., vol. 68(7), pp. 2760-2764.

* cited by examiner

Scheme 1.

PROTEASOME INHIBITING β-LACTAM COMPOUNDS

BACKGROUND OF THE INVENTION

Salinosporamide A (Compound 1) and omuralide (Compound 2) are potent naturally derived substances which inhibit proteasome function with very high selectivity. See references (1), (2), and (3).

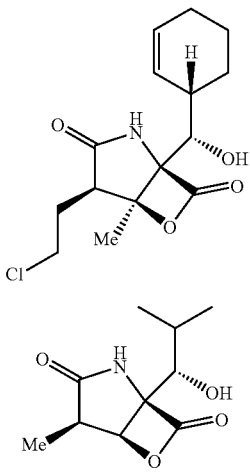

Proteasome inhibition offers considerable promise in the therapy of a number of types of cancer and is already used for multiple myelonoma. See reference (4). Several routes have been developed for the syntheses of Compounds 1 and 2. See references (1) and (5). One potential problem with the use of Compounds 1 or 2 as therapeutic agents is their short half-life in solution at pH 7 or in serum (estimated as low as 5-10 min). Because of this potential shortcoming, we have developed a synthesis of the β-lactam—Compound 3, which, to date has been found to be much more stable than the corresponding β-lactone (or either of Compounds 1 and 2).

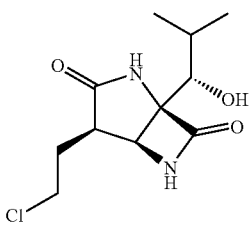

SUMMARY OF THE INVENTION

Thus, the present invention is directed to Compound 3, and to methods of preparing the compound and analogs thereof.

The preferred pathway of the synthesis of Compound 3 is outlined FIG. 1, which provides the preferred synthetic reaction sequences, referred to herein as Scheme 1.

In addition to Compound 3 per se, a preferred embodiment of the present invention is directed to the following method for the synthetic formation of Compound 3:

namely, the steps of:

(a) conversion of the alcohol, Compound 4, to the oxazolidinone, Compound 5:

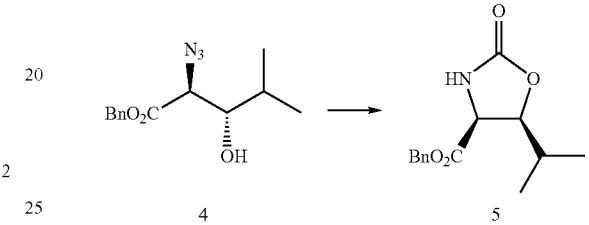

(b) N-protection of Compound 5 to generate Compound 6:

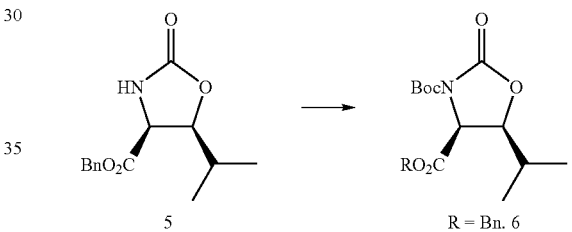

(c) cleavage of the benzyl ester subunit in Compound 6 to provide the carboxylic acid Compound 7:

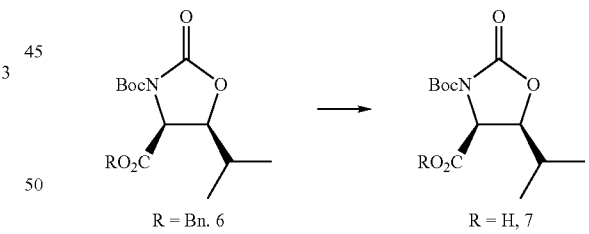

(d) reaction of Compound 7 with Compound 8 to form the β-lactam, Compound 9:

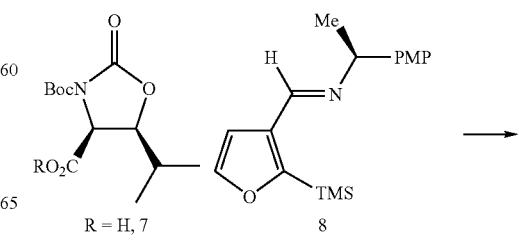

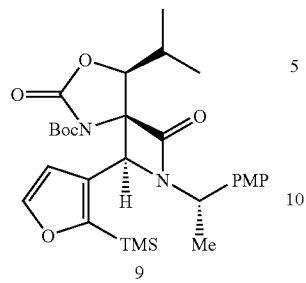
5
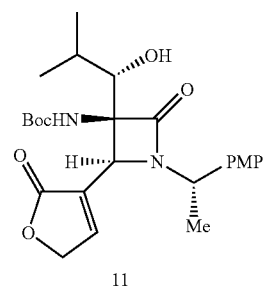
11
(e) cleavage of the oxazolidinone ring in Compound 9 to afford the alcohol 10:
(g) catalytic reduction of Compound 11 to provide the butyrolactone, Compound 12:
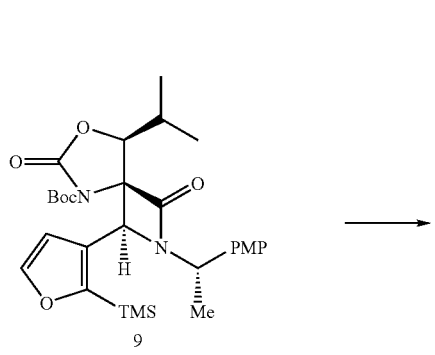
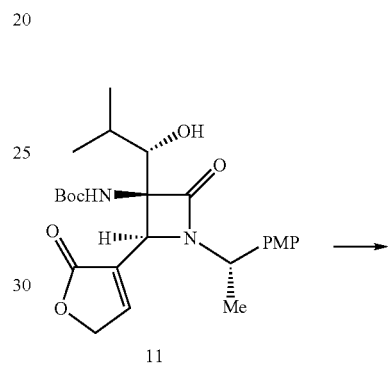
11
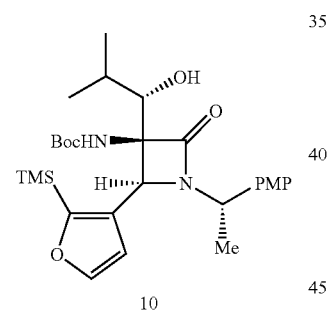
10
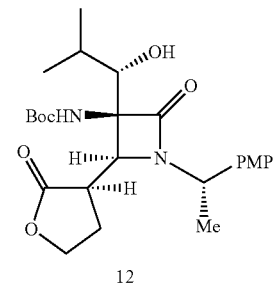
12
(f) oxidation of the 2-trimethsilylfuran subunit in Compound 10 to give the butenolide, Compound 11:
(h) cleavage of the t-butoxycarboxyl group of Compound 12 to provide the butyrolactam, Compound 13:
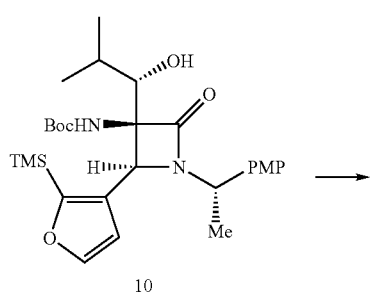
10
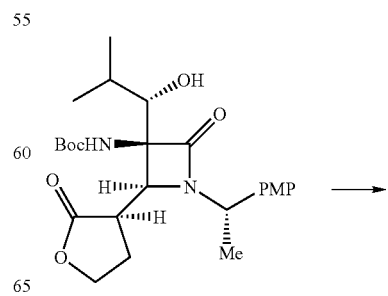
12

-continued

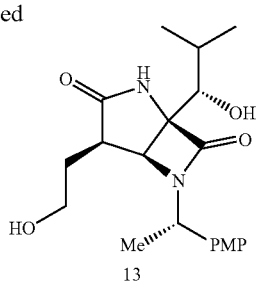

13

(i) changing the primary hydroxyl atom of Compound 13 to chlorine, to give Compound 14:

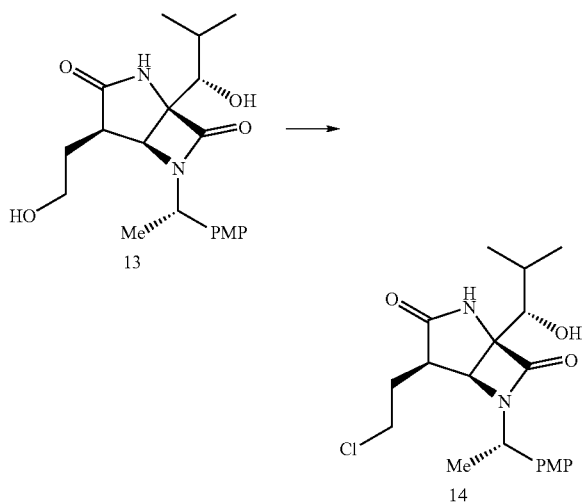

and (j) oxidative cleavage of the (S)(−)-(4-methoxyphenyl)-ethylamide protecting group in Compound 14 to give the β-lactam, Compound 3:

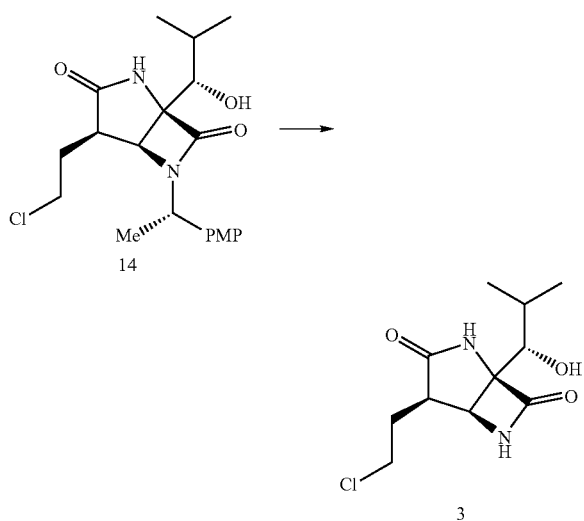

Two additional preferred embodiments of the present invention are pharmaceutical compositions comprising Compound 3, and methods of treatment of disease states in mammals, particularly humans, by the administration of a therapeutically effective amount of Compound 3 to a patient in need thereof.

Yet another preferred embodiment of the present invention is analogs and derivatives of Compound 3, prepared by synthetic and semi-synthetic techniques that are well known to those having ordinary skill in the art. Such compounds are represented by the following generic formula:

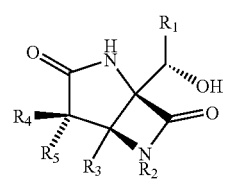

wherein:

$R_1$ is a cyclolower alkyl group, preferably one of the group consisting of cyclopropyl, cyclobutyl, cyclopentyl, cyclohexyl and cycloheptyl; or $R_1$ is a lower alkyl group, preferably one of the group consisting of methyl, ethyl, propyl, isopropyl, butyl, isobutyl, tert-butyl, and the like; and $R_2$ is a lower alkyl group, preferably one of the group consisting of methyl, ethyl, propyl, isopropyl, butyl, isobutyl, tert-butyl, and the like; and $R_3$ is either hydrogen or a lower alkyl group, preferably methyl; and $R_4$ a halo-lower alkyl group, preferably one of the group consisting of chloro-, bromo-, or iodo-ethyl, propyl, isopropyl, butyl, isobutyl, tert-butyl, and the like; and $R_5$ is either hydrogen or a lower alkyl group, preferably methyl.

These compounds can be prepared by appropriate modification of the intermediates employed in Scheme 1 for the formation of Compound 3, and by other synthetic modifications well known to those having ordinary skill in this art.

DETAILED DESCRIPTION OF THE INVENTION

Figures 1, 1A:
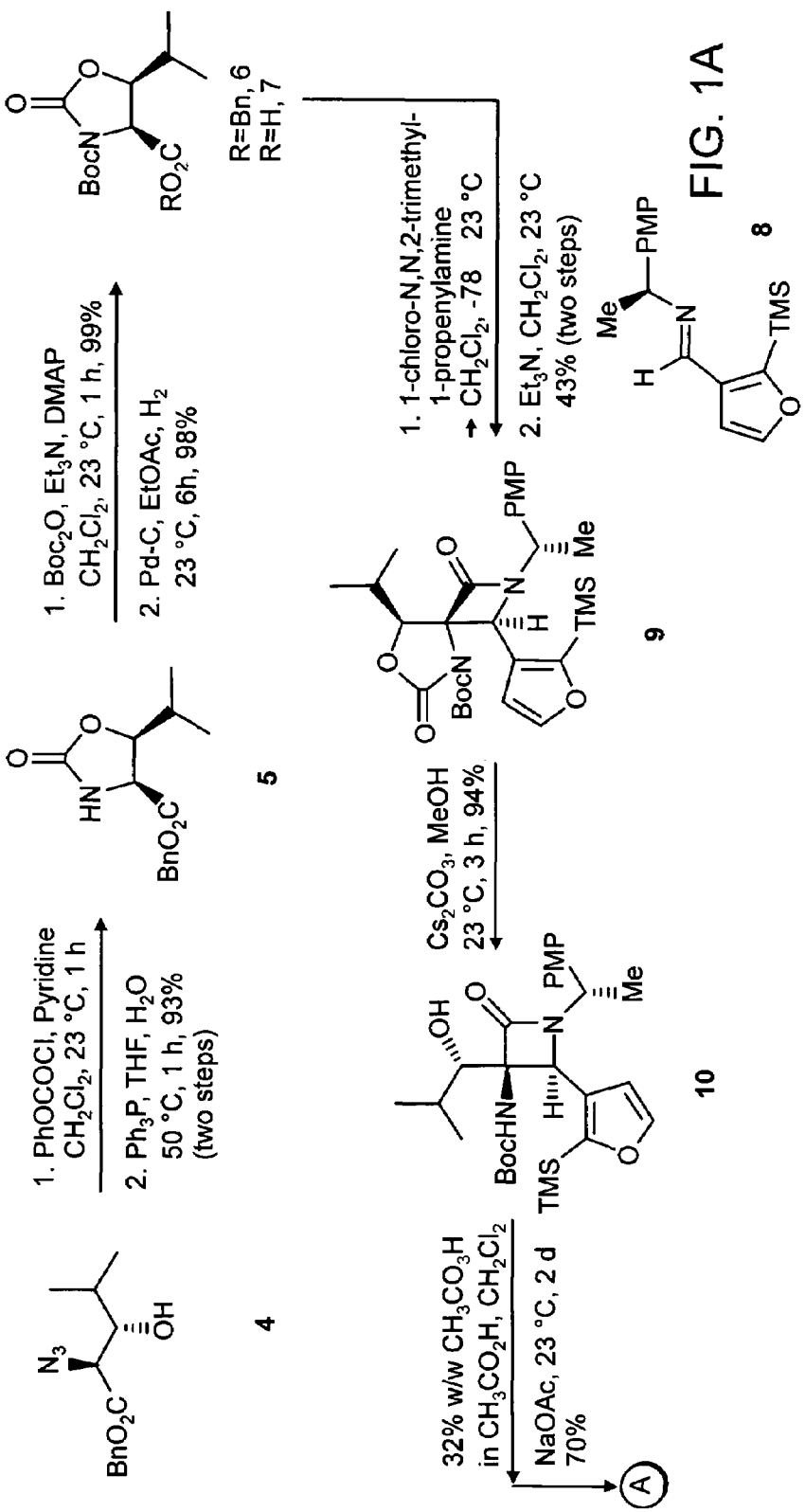
FIG. 1 shows Scheme 1, the preferred synthetic route to Compound 3, also known as β-lactam 3.
Figure 1B:
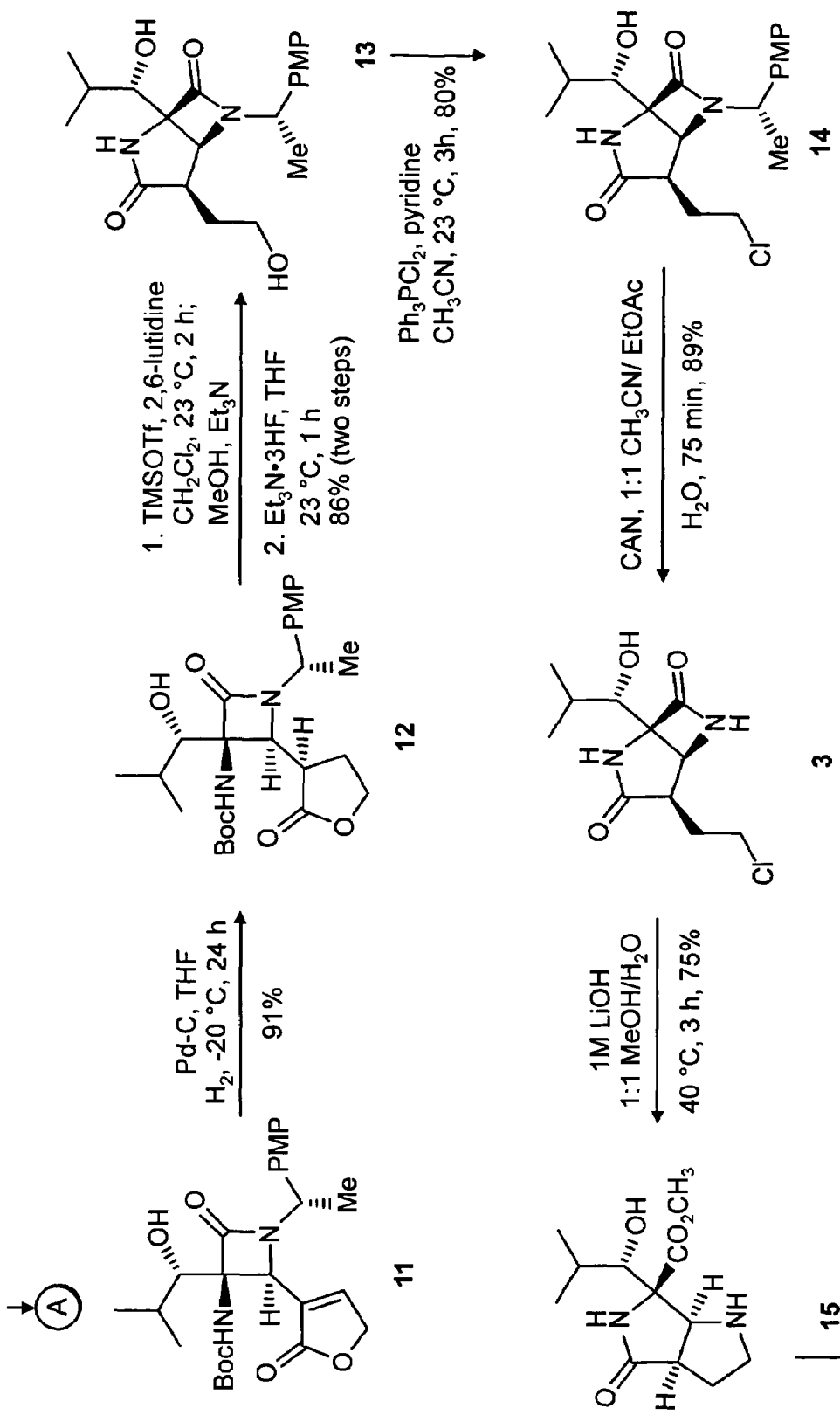

As shown in Scheme 1, the known alcohol Compound 4 (see reference (6)) was converted to the oxazolidinone, Compound 5 (93% yield) by successive acylation with phenyl chloroformate and pyridine in dichloromethane and reduction of the azide function with concomitant cyclization. N-Protection of Compound 5 with t-butylpyrocarbonate afforded Compound 6. Reductive cleavage of the benzyl ester subunit in Compound 6 provided the carboxylic acid Compound 7.

Addition of a solution of Compound 7 to a solution of 1-chloro-N,N-2-trimethyl-propenylamine (see reference (7))

led to smooth formation of the corresponding acid chloride. Rapid addition of the acid chloride to a mixture of the imine, Compound 8 (see reference (8)) and triethylamine gave stereoselectively the β-lactam, Compound 9, in 43% yield. Noteworthy in this transformation is the use of an imine derived from (S)-(−)-(4-methoxyphenyl)ethylamine. The corresponding imine derived from 4-methoxy-benzylamine led to β-lactam but in lower yields (~12%). Cleavage of the oxazolidinone ring in Compound 9 was accomplished by exposure to $Cs_2CO$, MeOH to afford the alcohol 10 in high yield (94%). See reference (9).

Oxidation of the 2-trimethsilylfuran subunit in Compound 10 by peroxyacetic acid gave the butenolide, Compound 11. See reference (10). Catalytic reduction of Compound 11 provided the butyrolactone, Compound 12, in 91% yield, the remainder of the material being the corresponding diastereomer. Cleavage of the t-butoxycarboxyl group of Compound 12 was accomplished with trimethylsilyl trifluoromethane sulfonate and 2,6-lutidine in dichloromethane at 23° C. Any remaining trimethylsilyl trifluoro-methanesulfonate was quenched by addition of methanol and triethylamine to the reaction mixture. Fluoride treatment during workup provided the desired butyro-lactam, Compound 13, in 86% yield. The chlorine atom was introduced by selective reaction of the primary hydroxyl of Compound 13 with dichlorotriphenylphosphorane and pyridine in acetonitrile at 23° C. to give Compound 14 in 80% yield.

Oxidative cleavage of the (S)(−)-(4-methoxyphenyl)-ethylamide protecting group in Compound 14 cleanly afforded the β-lactam, Compound 3, in 89% yield. We are pleased to report that Compound 3 is completely stable at pH 7 and 23° C. for 24 h.

Proteosome Inhibition

Determination of the inhibitory activity of Compound 3 against the 20S proteasome (see reference 12) was carried out by a modification of the method reported by Dick et al. See reference 11. Incubation of 20S proteasome (0.5 µg/mL) with 3 at (10 µM and 30 µM) in pH 7.9 buffer (20 mM Hepes, 0.5 mM E.DTA, 0.025% w/v SDS) at 37° C. resulted in a time dependent loss in the proteasome's ability to hydrolyze Suc-Leu-Leu-Val-Tyr-AMC (50 µM). See reference 12. The progress of proteasome inactivation was determined by addition of Suc-LLVY-AMC to a 2 mL aliquot of the incubation experiment and monitoring the rate of production of free AMC by fluorescence spectrophotometry.

Figure 2:
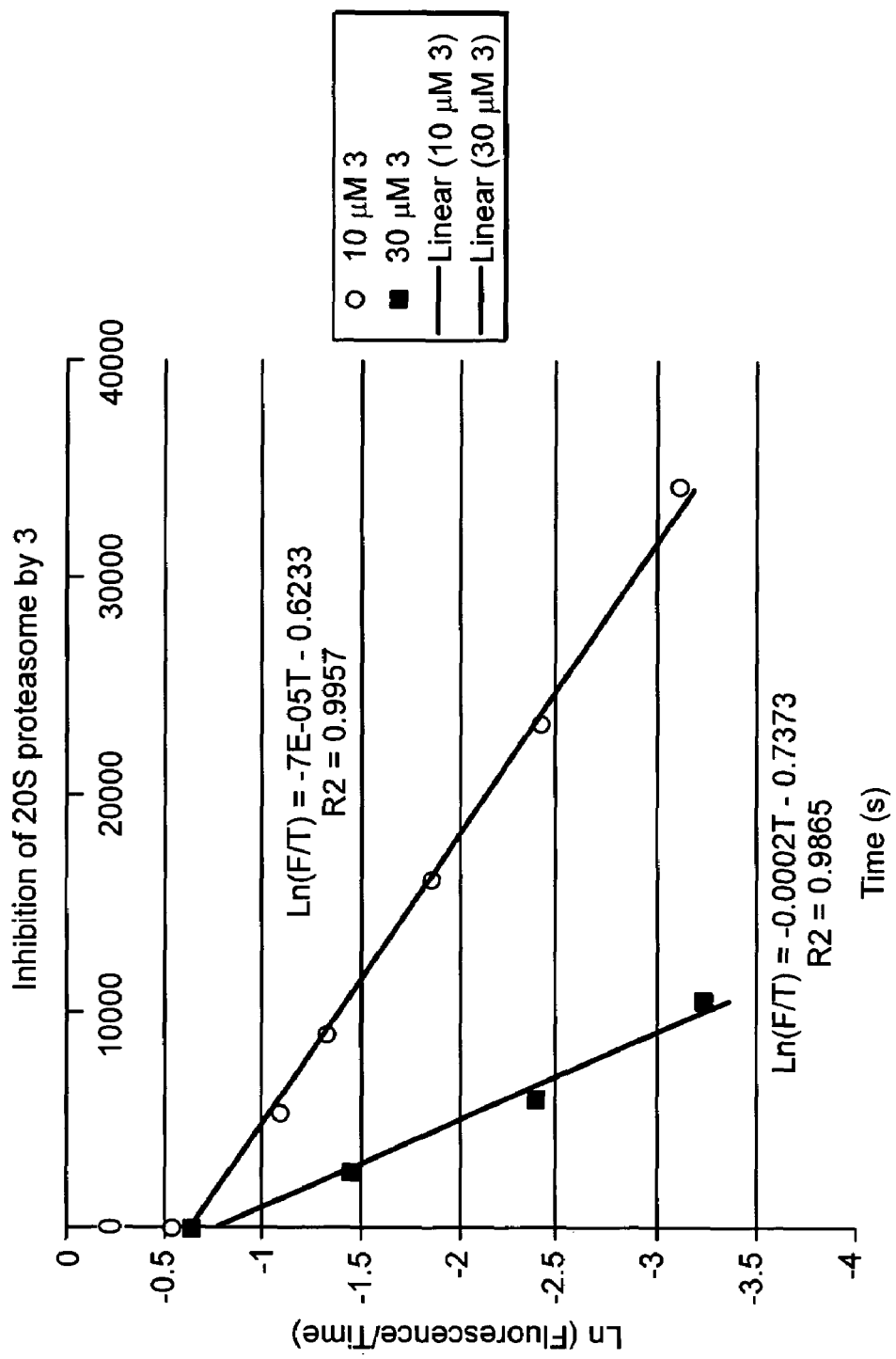
FIG. 2 illustrates a plot of ln (fluorescence/time) vs. time during proteasome inactivation experiments. The slope of these lines are equivalent to $k_{obs}$ for the inactivation of 20S proteasome by β-lactam 3. The half lives of inactivation of 20S proteasome by Compound 3 are approximately 58 and 165 min at concentrations of Compound 3 at 30 μM and 10 μM, respectively.

A plot of .ln(fluorescence/time) vs. time provided a linear decay whose slope is $k_{obs}$ for proteasome inactivation (FIG. 2). The rate of proteasome inactivation was proportional to the amount of Compound 3 present in the incubation experiments. The 10 µM and 30 µM time course experiments gave values for $k_{obs}/[3]$ as 7 M-1s-1 and 6.7 M-1s-1 respectively. In order to monitor background inactivation of 20S proteasome (see reference 13), each of these of experiments was run side by side with a control experiment identical in all respects except for the exclusion of Compound 3.

In the control experiment correlating to 30 µM 3, after 3 h, about 30% of initial proteasome activity was lost. In the control experiment correlating to 10 µM 3, after 9.5 h, about 50% of the initial proteasome activity remained. In each the corresponding experiments containing Compound 3, less than 10% of the initial proteasome activity remained at these respective time points.

It seems reasonable that the pathway of proteasome inhibition by the β-lactam 3 follows that of omuralide and salinosporamide A, i.e., acylation of a catalytically active threonine of a proteolytic β-subunit. It is likely also that this acylation is rendered irreversible by ring closure involving the chloroethyl group as an electrophile, as appears to be the case for salinosporamide A (see reference 5b), since treatment of 3 with methanolic base afforded the bicyclic pyrrolidine 15. This fact and the observation of proteasome inhibition in vitro suggest that Compound 3 is a worthy candidate for further biological evaluation.

Uses of Compound 3 and Analogs Thereof

The disclosed compounds may be used to treat conditions mediated directly by the proteolytic function of the proteasome such as muscle wasting, or mediated indirectly via proteins which are processed by the proteasome such as NF-kappa-B. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-kappa-B. Treating as used herein includes reversing, reducing, or arresting the symptoms, clinical signs, and underlying pathology of a condition in manner to improve or stabilize the subject's condition.

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain. Kojima, S. et al., Fed. Eur. Biochem. Soc., (1992) 304: 57-60. The APP-processing enzyme cleaves at the $Gln^{15}$—$Lys^{16}$ bond; in the presence of calcium ion, the enzyme also cleaves at the $Met^{-1}$-$Asp^1$ bond, and the $Asp^1$-$Ala^2$ bonds to release the extracellular domain of β-AP.

One embodiment, therefore, is a method of treating Alzheimer's disease, including administering to a subject an effective amount of a compound (e.g., pharmaceutical composition) having a formula disclosed herein. Such treatment includes reducing the rate of β-AP processing, reducing the rate of β-AP plaque formation, and reducing the rate of β-AP generation, and reducing the clinical signs of Alzheimer's disease.

Other embodiments of the invention relate to cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Proteasome inhibitors are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736 (1994). Embodiments of the invention therefore encompass methods for: reducing the rate of muscle protein degradation in a cell, reducing the rate of intracellular protein degradation, reducing the rate of degradation of p53 protein in a cell, and inhibiting the growth of p53-related cancers).

Each of these methods includes the step of contacting a cell (in vivo or in vitro, e.g., a muscle in a subject) with an effective amount of a compound (e.g., pharmaceutical composition) of a formula disclosed herein.

Another protein processed by the proteasome is NF-kappa-B, a member of the Rel protein family. The Rel family of transcriptional activator proteins can be divided into two groups. The first group requires proteolytic processing, and includes p50 (NF-kappa-B1, 105 kDa) and p52 (NF-kappa-2, 100 kDa). The second group does not require proteolytic processing, and includes p65 (RelA, Rel (c-Rel), and RelB). Both homo- and heterodimers can be formed by Rel family members; NF-kappa-B, for example, is a p50-p65 heterodimer. After phosphorylation and ubiquitination of Ikappa-B and p105, the two proteins are degraded and processed, respectively, to produce active NF-kappa-B which translocates from the cytoplasm to the nucleus. Ubiquitinated p105 is also processed by purified proteasomes. Palombella et al., Cell (1994) 78:773-785. Active NF-kappa-B forms a stereospecific enhancer complex with other transcriptional activators and, e.g., HMG I(Y), inducing selective expression of a particular gene.

NF-kappa-B regulates genes involved in the immune and inflammatory response, and mitotic events. For example, NF-kappa-B is required for the expression of the immunoglobulin light chain kappa-gene, the IL-2 receptor alpha-chain gene, the class I major histocompatibility complex gene, and a number of cytokine genes encoding, for example, IL-2, IL-6, granulocyte colony-stimulating factor, and IFN-β. Palombella et al., (1994). Some embodiments of the invention include methods of affecting the level of expression of IL-2, MHC-I, IL-6, IFN-β or any of the other previously-mentioned proteins, each method including administering to a subject an effective amount of a compound of a formula disclosed herein.

NF-kappa-B also participates in the expression of the cell adhesion genes that encode E-selectin, P-selectin, ICAm, and VCAM-1, Collins, T., Lab. Invest. (1993) 68:499-508. One embodiment of the invention is a method for inhibiting cell adhesion (e.g., cell adhesion mediated by E-selectin, P-selectin, ICAm, or VCAM-1), including contacting a cell with (or administering to a subject) an effective amount of a compound (e.g., pharmaceutical composition) having a formula disclosed herein.

NF-kappa-B also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of I-kappa-B, triggering Ikappa-B degradation through the ubiquitin-proteasome pathway. After degradation, NF-kappa-B is released into the nucleus, thus enhancing the transcription of HIV. Cohen, J., Science, (1995) 267:960. Two embodiments of the invention are a method for inhibiting or reducing HIV infection in a subject, and a method for decreasing the level of viral gene expression, each method including administering to the subject an effective amount of a compound of a formula disclosed herein.

Complexes including p50 are rapid mediators of acute inflammatory and immune responses. Thanos, D. and Maniatis, T., Cell (1995) 80:529-532. Intracellular proteolysis generates small peptides for presentation to T-lymphocytes to induce MHC class I-mediated immune responses. The immune system screens for autologous cells that are virally infected or have undergone oncogenic transformation. Two embodiments of the invention are a method for inhibiting antigen presentation in a cell, including exposing the cell to a compound of a formula described herein, and a method for suppressing the immune system of a subject (e.g., inhibiting transplant rejection), including administering to the subject an effective amount of a compound of a formula described herein.

In addition, the invention provides a method for treating inflammation, wherein the method includes administering to a subject an effective anti-inflammatory amount of a pharmaceutical composition containing a compound of a formula described herein. Inflammation can be a primary or secondary responses associated with (a) injury such as a cut, laceration, puncture wound, (b) infection (including infected surgical incisions) by one or more viruses, bacteria, mycobacteria, microorganisms, parasites, and fungi, (c) allergies, (d) a disease state, (e) surgery (e.g., transplantation), or (f) a combination thereof.

Allergies are primary inflammatory responses to antigens or allergens. Sources of allergens include plants (e.g., grass or tree pollen), animals (e.g., dander, venom, urine, execreta from dogs, cats, insects, and snakes), and fungi. In addition to allergens such as rye grass, ragweed, and Japanese cedar pollen, certain foods or food components (e.g., eggs, milk, shellfish, strawberries, chocolate), vaccines, and drugs (e.g., penicillin) can induce allergic reactions in certain individuals.

Disease states include rheumatoid arthritis, scleroderma, rheumatic fever, inflammatory bowel disease (e.g., Crohn's disease and ulcerative colitis), diabetes mellitus, myasthenia gravis, multiple sclerosis, Guillain-Barre syndrome, conjuctiva of the eye, systemic lupus erythematosus, encephalitis, Adult Respiratory Distress Syndrome, psoriasis, emphysema, Alzheimer's disease, and muscular dystrophy.

The invention provides a method of treating inflammation induced by organ or tissue transplantation. This method includes administering to a patient who has undergone or is about to undergo transplantation a composition containing a compound having a formula disclosed herein. Transplantations include bone marrow, solid organ (e.g., kidney, lungs, heart, pancreas, liver, and skin), or tissues.

Certain proteasome inhibitors block both degradation and processing of ubiquitnated NF-kappa-B in vitro and in vivo. Proteasome inhibitors also block Ikappa-B-alpha degradation and NF-kappa-B activation, Palombella, et al.; and Traenckner, et al., EMBO J. (1994) 13:5433-5441. One embodiment of the invention is a method for inhibiting Ikappa-B-alpha degradation, including contacting the cell with a compound of a formula described herein. A further embodiment is a method for reducing the cellular content of NF-kappa-B in a cell, muscle, organ, or subject, including contacting the cell, muscle, organ, or subject with a compound of a formula described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a compound of a formula disclosed herein. Cyclins are proteins involved in cell cycle control. The proteasome participates in the degradation of cyclins. Examples of cyclins include mitotic cyclins, G1 cyclins, (cyclin B). Degradation of cyclins enables a cell to exit one cell cycle stage (e.g., mitosis) and enter another (e.g., division). It is believed all cyclins are associated with p34.sup.cdc2 protein kinase or related kinases. The proteolysis targeting signal is localized to amino acids 42-RAALG- NISEN-50 (destruction box). There is evidence that cyclin is converted to a form vulnerable to a ubiquitin ligase or that a cyclin-specific ligase is activated during mitosis. Ciechanover, A., Cell, (1994) 79:13-21. Inhibition of the proteasome inhibits cyclin degradation, and therefore inhibits cell proliferation (e.g., cyclin-related cancers). Kumatori et al., Proc. Natl. Acad. Sci. USA (1990) 87:7071-7075. One embodiment of the invention is a method for treating a proliferative disease in a subject (e.g., cancer, psoriasis, or restenosis), including administering to the subject an effective amount of a compound of a formula disclosed herein. Chronic or acute inflammation can result from transplantation rejection, arthritis, rheumatoid arthritis, infection, dermatosis, inflammatory bowel disease, asthma, osteoporosis, and autoimmune diseases. Rejection or inflammation can occur in transplanted tissues or organs of any type, including heart, lung, kidney, liver, skin grafts, and tissue grafts. The invention also encompasses a method for treating cyclin-related inflammation in a subject, including administering to a subject an effective amount of a compound of a formula described herein.

Additional embodiments are methods for affecting the proteasome-dependent regulation of oncoproteins and methods of treating or inhibiting cancer growth, each method including exposing a cell (in vivo, e.g., in a subject or in vitro) to a compound of a formula disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a compound of a formula disclosed herein.

Treatment of cancer prevents, alleviates, or ameliorates one or more primary or secondary phenomena associated with the initiation, progression, and metastasis of tumors, especially malignant tumors, e.g., a growth of tissue wherein cell multiplication is uncontrolled. Malignant tumors show a greater degree of anaplasia than do benign tumors. The invention provides a method of treating cancer including administering to a subject an effective anti-cancer amount of a pharmaceutical composition described herein, wherein the cancer is selected from carcinoma, lymphoma, sarcoma, and myeloma.

Examples of carcinomas include adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Examples of sarcoma include amelioblastic sarcoma, angiolithic sarcoma, botryoid sarcoma, endometrial stroma sarcoma, ewing sarcoma, fascicular sarcoma, giant cell sarcoma, granulocytic sarcoma, immunoblastic sarcoma, juxaccordial osteogenic sarcoma, coppices sarcoma, leukocytic sarcoma (also known as leukemia), lymphatic sarcoma (also known as lympho sarcoma), medullary sarcoma, myeloid sarcoma (also known as granulocytic sarcoma), austiogenci sarcoma, periosteal sarcoma, reticulum cell sarcoma (also known as histiocytic lymphoma), round cell sarcoma, spindle cell sarcoma, synovial sarcoma, and telangiectatic audiogenic sarcoma. Examples of lymphomas include Hodgkin's disease and lymphocytic lymphomas, such as Burkitt's, nodular poorly-differentiated lymphocytic (NPDL), nodular mixed lymphocytic (NML), NH (nodular histiocytic), and diffuse lymphomas. Additional carcinomas include neural blastoma, glioblastoma, astrocytoma, melanoma, leiomyo sarcoma, multiple myeloma, and Hemangioma.

A tripeptide aldehyde protease inhibitor (benzyloxycarbonyl (Z)-Leu-Leu-leucinal induces neurite outgrowth in PC12 cells at an optimal concentration of 30 nM, Tsubuki et al., Biochem. and Biophys. Res. Comm. (1993) 196:1195-1201. Peptide aldehydes have been shown to inhibit the chymotryptic activity of the proteasome. Vinitsky, et al., 1992, Tsubuki et al., 1993. One embodiment of the invention is a method of promoting neurite outgrowth, including administering to the subject a compound of a formula disclosed herein.

Finally, the disclosed compounds are also useful as diagnostic agents (e.g., in diagnostic kits or for use in clinical laboratories) for screening for proteins (e.g., enzymes, transcription factors) processed by the proteasome. The disclosed compounds are also useful as research reagents for specifically binding the X/MB1 subunit or alpha.-chain and inhibiting the proteolytic activities associated with it. For example, the activity of (and specific inhibitors of) other subunits of the proteasome can be determined.

Most cellular proteins are subject to proteolytic processing during maturation or activation. Compound 3 can be used to determine whether a cellular, developmental, or physiological process or output is regulated by the proteolytic activity of the proteasome. One such method includes obtaining an organism, an intact cell preparation, or a cell extract; exposing the organism, cell preparation, or cell extract to a compound of a formula disclosed herein; exposing the compound-exposed organism, cell preparation, or cell extract to a signal, and monitoring the process or output. The high selectivity of the compounds disclosed herein permits rapid and accurate elimination or implication of the proteasome in a given cellular, developmental, or physiological process.

The compounds and compositions of the invention are useful in several methods including a method of treating inflammation, comprising administering to a subject an effective anti-inflammatory amount of a pharmaceutical composition described herein; wherein the inflammation is associated with injury or infection; wherein the inflammation is associated with an allergy or asthma; wherein the inflammation is associated with a disease state selected from rheumatoid arthritis, scleroderma, rheumatic fever, inflammatory bowel disease, diabetes mellitus, myasthenia gravis, multiple sclerosis, Guillan-Barre syndrome, conjunctiva of the eye, systemic lupus erythematosus, encephalitis, Adult Respiratory Distress Syndrome, emphysema, Alzheimer's disease, and muscular dystrophy; wherein the inflammation is associated with transplantation of bone marrow or a solid organ selected from kidney, lung, heart, pancreas, liver, and skin, and the composition is administered before, during, or after transplantation; wherein the pharmaceutical composition is administered orally; or combinations thereof.

The invention also provides a method of treating cancer, comprising administering to a subject an effective anti-cancer amount of a pharmaceutical composition described herein; a method for treating psoriasis, comprising administering to a subject an effective amount of a pharmaceutical composition described herein; and a method for treating restenosis, comprising administering to a subject an effective amount of a pharmaceutical composition described herein.

Formulation and Administration

The methods of the invention contemplate treatment of animal subjects, such as mammals (e.g., higher primates, and especially humans). The invention encompasses pharmaceutical compositions which include novel compounds described herein, and pharmaceutical compositions which include compounds described and first recognized herein as proteasome inhibitors such as Compound 3.

Pharmaceutically acceptable salts may be formed, for example, with 1, 2, 3, or more equivalents of hydrogen chloride, dihydrogen bromide, trifluoroacetic acid, and others known to those in the art of drug formulation. Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as anti-inflammatory, anti-cancer, or other agents. A subject may have more than one type of inflammation, or more than one type of cancer, a combination of allergies, or a mixture of the above conditions for which the disclosed compounds are useful. A compound of the invention may be administered in unit dosage form, and may be prepared by any of the methods well known in the pharmaceutical art, for example, as described in Remington's Pharmaceutical Sciences (Mack Pub. Co., Easton, Pa., 1980). The invention also encompasses a packaged drug, containing a pharmaceutical composition formulated into individual dosages and printed instructions for self-administration.

Compounds disclosed herein as proteasome inhibitors may be prepared for use in parenteral administration in the form of solutions or liquid suspensions; for oral administration (preferable), particularly in the form of tablets or capsules; or intranasally, particularly in the form of powders, gels, oily solutions, nasal drops, aerosols, or mists. Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactide/glycolide or polyoxyethylene/polyoxypropylene.

Additional parental delivery systems include ethylene-vinyl acetate copolymer particles, osmotic pumps, implantable infusion systems, and liposomes. Formulations for inhalation administration contain lactose, polyoxyethylene-9-lauryl ether, glycocholate, or deoxycholate. Formulations for buccal administration may include glycocholate; formulations for vaginal administration may include citric acid.

The concentration of a disclosed compound in a pharmaceutically acceptable mixture will vary depending on several factors, including the dosage of the compound to be administered, the pharmacokinetic characteristics of the compound(s) employed, and the route of administration. In general, the compounds of this invention may be provided in an aqueous physiological buffer solution containing about 0.1-10% w/v of compound for parenteral administration.

Typical dose ranges are from about 0.1 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

The effective amount of the active compound used to practice the present invention for treatment of conditions directly or indirectly mediated by the proteasome varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as "effective amount".

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

General. All moisture sensitive reactions were performed under nitrogen gas in glassware that was flame-dried and equipped with a magnetic stir bar. Tetrahydrofuran (THF) and was freshly distilled from sodium benzophenone ketyl before use. Hexanes, pyridine, triethylamine, pentane and dichloromethane were freshly distilled from $CaH_2$ before use. Toluene was distilled from sodium. Thin-layer chromatography (TLC) was performed using E. Merck silica gel 60 F254 pre-coated plates (0.25 mm). Flash chromatography was performed using Baker silica gel (40 μm particle size). All products were purified to homogeneity by TLC analysis (single spot/two solvent systems) using a UV lamp or CAM or PMA or anisaldehyde or basic KMnO4 for detection purposes. NMR spectra were recorded on 400 MHz, 500 MHz and 600 MHz spectrometers. $^1H$ and $^{13}C$ NMR chemical shifts are reported as δ using residual solvent as an internal standard. High-resolution mass spectral analyses were performed at Harvard University Mass Spectrometry Center. Fluorescence spectrophotometry was performed on a Perkin Elmer LS 50B Luminescence Spectrometer equipped with a heating coil and stirring apparatus.

EXAMPLE 1

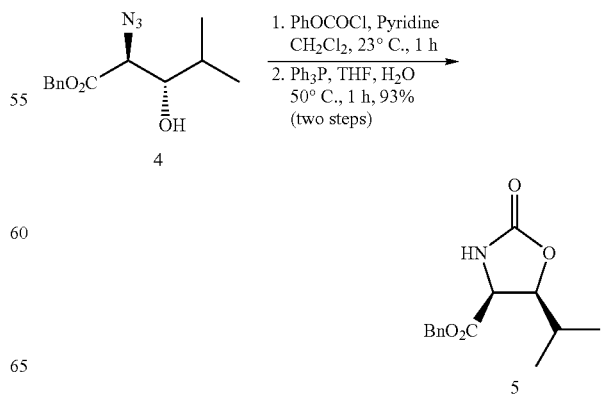

(4S,5S) 5-Isopropyl-2-oxo-oxazolidine-4-carboxylic acid benzyl ester (Compound 5). To a solution of the azide, Compound 4 (prepared essentially by the method of Hruby et al., J. Org. Chem. 2002, 67, 3514-3517) (2.0 g, 7.6 mmol, 1 equiv) in dichloromethane at 23° C. (20 mL), was added pyridine (920 μL, 11.5 mmol, 2.5 equiv), followed by phenyl chloroformate (1.05 mL, 8.35 mmol, 1.1 equiv). After 1 h the resulting suspension was partitioned between dichloromethane (50 ml) and aqueous hydrochloric acid (2N, 50 mL). The organics were dried over sodium sulfate and concentrated in vacuo. To the resultant residue was added THF (20 mL), water (2 mL) and triphenylphosphine (2.2 g, 8.35 mmol, 1.1 equiv). The resulting solution was heated to 50° C. for 1 h, during which time gas evolution was observed. The reaction was diluted with dichloromethane (100 mL) and sodium sulfate was added to the resultant solution. The organics were filtered and concentrated in vacuo. The residue was purified by flash chromatography on silica gel, gradient elution (40-50-60-70% ethyl acetate in hexanes) to give the oxazolidinone, Compound 5 (1.85 g, 7.1 mmol, 93%) as a colorless solid mp=99-101° C., $R_f$=0.29 (50% ethyl acetate in hexanes), $[\alpha]^{23}_D$ −12.5 (c 1.15, CHCl$_3$); FTIR (neat), cm$^{-1}$: 3288, 2971, 1762, 1739, 1214; $^1$H NMR (500 MHz, CDCl$_3$), δ: 7.37 (m, 5H), 5.71 (bs, 1H), 5.22 (ABQ, 2H, J=12 Hz), 4.37 (m, 1H), 1.76 (m, 1H), 0.97 (d, 3H, J=6.5 Hz), 0.92 (d, 3H, J=7 Hz); $^{13}$C NMR (100 MHz, CDCl$_3$), δ: 169.4, 159.5, 134.6, 128.7, 128.6, 128.6, 67.6, 58.0, 29.0, 18.7, 18.4. LRMS Calcd for C$_{14}$H$_{17}$NO$_4$ [M]$^+$ 263.1. Found [M+NH$_4$]$^+$ 281.2.

EXAMPLE 2

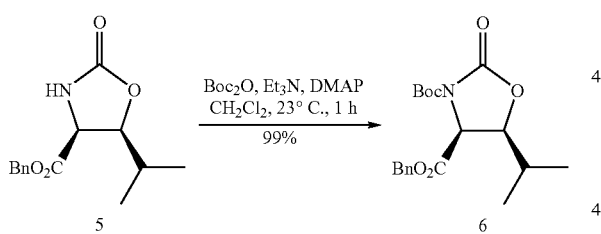

(4S,5S) 5-Isopropyl-2-oxo-oxazolidine-3,4-dicarboxylic acid 4-benzyl ester 3-tertbutyl ester (Compound 6). To a solution of the oxazolidinone 5 (1.85 g, 7.1 mmol, 1 equiv) in dichloro-methane (20 mL) was added triethylamine (1.5 mL, 10.1 mmol, 1.5 equiv), di-tent-butyl dicarbonate (1.69 g, 7.8 mmol, 1.1 equiv) and 4-dimethylaminopyridine (86 mg, 710 μmol, 0.1 equiv). The resultant mixture was allowed to stir at 23° C. for 1 h. The reaction was concentrated in vacuo. The residue was purified by flash chromatography on silica gel (35% ethyl acetate in hexanes) to give 6 (2.56 g, 7.05 mmol, 99%) as a colorless solid mp 114-115° C., $R_f$=0.39 (25% ethyl acetate in hexanes), $[\alpha]^{23}_D$ −38.4 (c 0.95, CHCl$_3$); FTIR (neat), cm$^{-1}$: 2891, 2937, 1825, 1746, 1727, 1358, 1212, 1075; $^1$H NMR (500 MHz, CDCl$_3$), δ: 7.36 (m, 5H), 5.23 (d, 1H, J=12.5 Hz), 5.19 (d, 1H, J=12.5 Hz), 4.71 (d, 1H, J=7.5 Hz), 4.13 (dd, 1H, J=7, 5 Hz), 1.64 (m, 1H), 1.41 (s, 9H0, 1.01 (d, 3H, J=6.5 Hz), 0.93 (d, 3H, J=6.5 Hz); $^{13}$C NMR (100 MHz, CDCl$_3$), δ: 167.5, 151.2, 148.3, 128.7, 128.6, 128.4, 84.2, 80.4, 67.4, 60.5, 28.8, 27.5, 18.2, 18.0. LRMS Calcd for C$_{19}$H$_{25}$NO$_6$ [M]$^+$ 363.2. Found [M+NH$_4$]$^+$381.3.

EXAMPLE 3

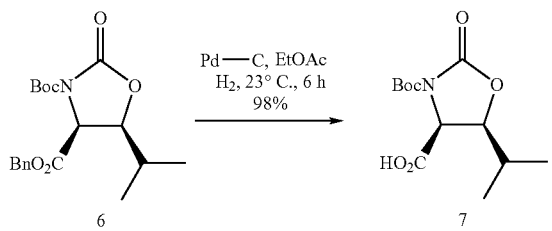

(4S,5S) 5-Isopropyl-2-oxo-oxazolidine-3,4-dicarboxylic acid 3-tert-butyl ester (Compound 7). To a solution of the benzyl ester 6 (2.56 g, 7.05 mmol, 1 equiv) in ethyl acetate (100 mL) was added 10% Pd on carbon (500 mg), and the solution was placed under a balloon atmosphere of hydrogen. The suspension was stirred for 6 h, at which time the suspension was filtered through Celite and concentrated in vacuo to give the acid 7 (1.38 g, 6.91 mmol, 98%) as a colorless solid mp 120-122° C., $R_f$=0.2 (50% ethyl acetate in hexanes), $[\alpha]^{23}_D$ −24.7 (c 0.97, CHCl$_3$; FTIR (neat), cm$^{-1}$: 3502, 3205, 2981, 1806, 1729, 1368, 1216; $^1$H NMR (500 MHz, CDCl$_3$), δ: 4.74 (d, 1H, J=7 Hz), 4.19 (dd, 1H, J=7.5, 5 Hz), 1.90 (m, 1H), 1.521 (s, 9H), 1.01 (d, 3H, J=6 Hz), 1.06 (d, 3H, J=6 Hz); $^{13}$C NMR (100 MHz, CDCl$_3$), δ: 171.9, 151.9, 85.0, 80.6, 60.6, 29.0, 27.7, 19.0, 18.3; LRMS Calcd for C$_{12}$H$_{19}$NO$_6$ [M]$^+$ 273.1. Found [M+NH$_4$]$^+$291.2.

EXAMPLE 4

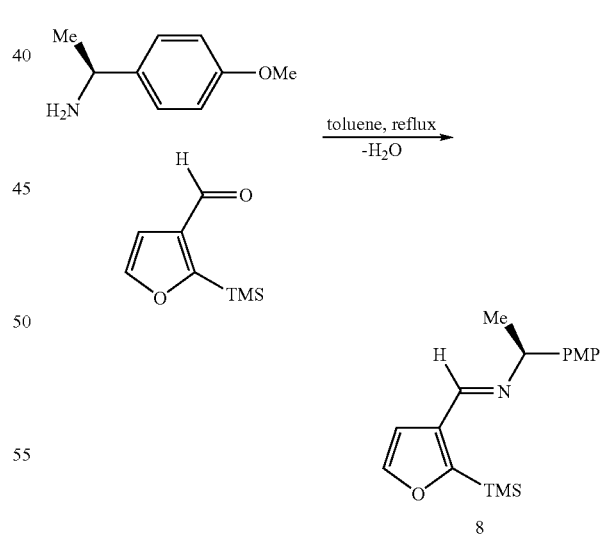

Imine—Compound 8. To a solution of 2-trimethylsilyl-3-furaldehyde* (176 mg, 1.05 mmol, 1.05 equiv) in toluene (12 mL) in a 25 mL round-bottomed flask was added (S)-(−)-(4methoxyphenyl)ethylamine (148 μL, 1.0 mmol, 1 equiv). A Dean Stark trap was affixed to the apparatus, and the resulting solution was refluxed with concomitant removal of water (10 min). The solution was concentrated in vacuo. The imine 8 was judged to be sufficiently pure (about 90% by $^1$H NMR) to be used without further purification. $^1$H NMR (400 MHz, CDCl$_3$), δ: 8.36 (s, 1H), 7.56 (bs, 1H), 7.31 (d, 2H, J=9 Hz), 6.89 (d, 2H, J=8.5 Hz), 6.86 (bs, 1H), 4.44 (q, 1H, J=7 Hz), 3.80 (s, 3H), 1.55 (d, 3H, J=7 Hz), 0.31 (s, 9h).

*See, Denat, F.; Gaspard-lloughmane, H.; Dubac, J. Synthesis 1992, 10, 145-146.

EXAMPLE 5

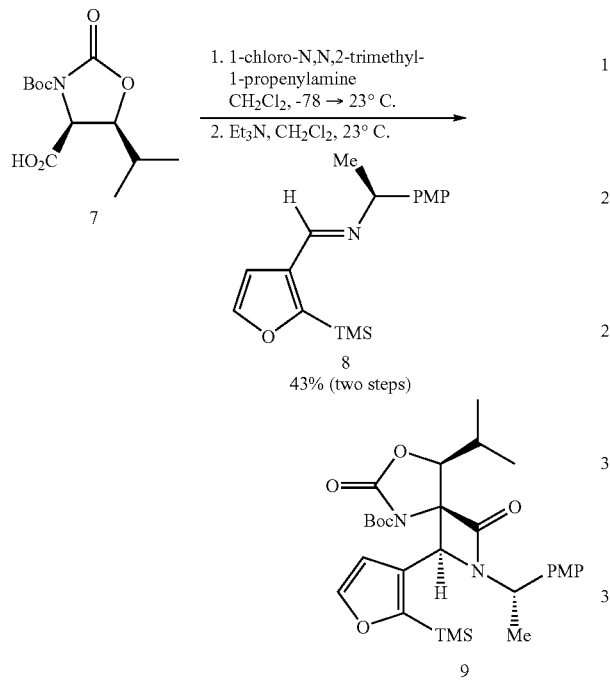

β-lactam 9. A solution of the acid Compound 7 (273 mg, 1 mmol, 1 equiv) in dichloromethane (5 mL) was added dropwise slowly via cannula to a solution of 1-chloro-N,N,2-trimethyl-1propenylamine* (331 μL, 2.5 mmol, 2.5 equiv) in dichloromethane (10 mL) at −78° C. The resultant solution was allowed to warm to 23° C. and stirred for 0.5 h. The solution was concentrated in vacuo. To the residue was added dichloromethane (2.5 mL), and the resultant solution was added quickly via cannula transfer to a mixture of freshly prepared imine, Compound 8 (1 mmol, 1 equiv) and triethylamine (420 μL, 3.0 mmol, 3 equiv). The resultant suspension was allowed to stir for 0.5 h at 23° C. at which time the reaction was partitioned between ethyl acetate (100 mL) and aqueous hydrochloric acid (2N, 50 mL). The organics were dried over sodium sulfate and concentrated in vacuo. The residue was purified by flash chromatography on silica gel (gradient elution 2-4-6-8-10% diethyl ether in 1:1 dichloromethane/hexanes) to give the β-lactam, Compound 9 (240 mg, 0.43 mmol, 43%). R$_f$=0.47 (40% ethyl acetate in hexanes), [α]$^{23}$$_D$+60.61 (c 0.815, CHCl$_3$); FTIR (neat), cm$^{-1}$: 2968, 1804, 1767, 1735, 1515; $^1$H NMR (500 MHz, CDCl$_3$), δ: 7.53 (d, 1H, J=1 Hz), 7.14 (d, 2H, J=8.5 Hz), 6.86 (d, 2H, J=8.5 Hz), 6.60 (d, 1H, J=1 Hz), 5.20 (q, 1H, J=7 Hz), 4.39 (s, 1H), 4.17 (d, 1H, J=3 Hz), 3.80 (s, 3H), 2.19 (m, 1H), 1.52 (s, 9H), 1.46 (d, 3H, J=7 Hz), 1.03 (d, 3H, J=7 Hz), 0.99 (d, 3H, J=7 Hz), 0.14 (s, 9h); $^{13}$C NMR (100 MHz, CDCl$_3$), δ: 162.0, 159.6, 159.3, 150.8, 148.8, 146.5, 146.4, 131.2, 129.3, 128.7, 114.4, 111.4, 85.2, 85.1, 63.2, 55.5, 51.3, 31.4, 28.0, 19.6, 18.8, 15.7, −1.0; HRMS (ES+) Calcd for C$_{92}$H$_{41}$N$_2$O$_7$Si [MH]$^+$ 557.2683. Found 557.2961.

* For a convenient preparation, see: Ghosez, L.; George-Koch, I.; Pating, L.; Houtekie, M.; Bovy, P.; Nshimyumuzika, P.; Phan, T. Tetrahedron 1998, 54, 9207-9222.

EXAMPLE 6

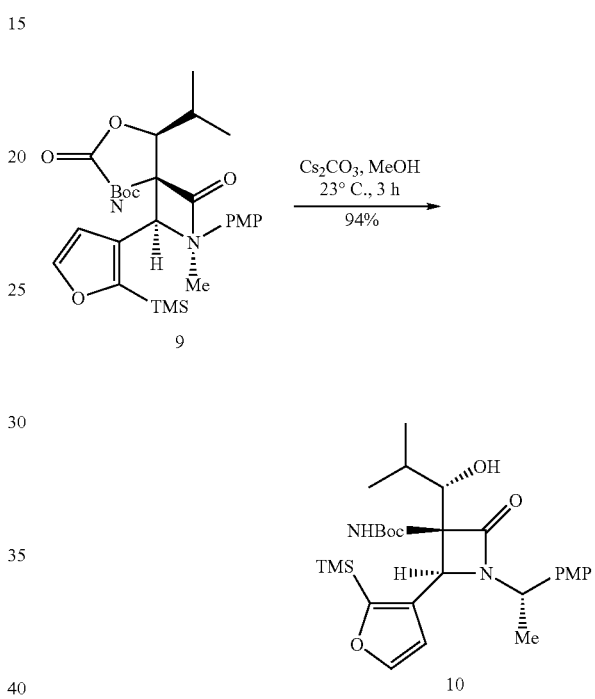

Alcohol—Compound 10. To a solution of the β-lactam 9 (1.08 g, 1.94 mmol, 1 equiv) in methanol (10 mL) was added cesium carbonate* (1.0 g, 3.07 mmol, 2.84 equiv). The resultant solution was allowed to stir at 23° C. for 2 h, at which time the reaction was partitioned between ethyl acetate (200 mL) and water (30 mL). The organics were dried over sodium sulfate and concentrated in vacuo. The resultant residue was purified by flash chromatography on silica gel (gradient elution 20-30-40% ethyl acetate in hexanes) to afford Compound 10 (971 mg, 1.83 mmol, 94%). R$_f$=0.61 (50% ethyl acetate in hexanes). [α]$^{23}$$_D$+15.60 (c 0.795, CHCl$_3$ FTIR (neat), cm$^{-1}$: 3284, 2962, 1735, 1688; $^1$H NMR (500 MHz, CDCl$_3$), δ: 7.57 (d, 1H, J=1 Hz), 7.14 (d, 2H, J=9 Hz), 6.85 (d, 2H, J=9 Hz), 6.51(d, 1H, J=1 Hz), 5.82 (s, 1H), 5.41 (d, 1H, J=11 Hz), 4.98 (q, 1H, J=7 Hz), 4.94 (s, 1H), 3.80 (s, 3H), 3.40 (dd, 1H, J=5, 11 Hz), 1.89 (m, 1H), 1.38 (d, 3H, J=7 Hz), 1.17 (s, 9H), 1.02 (d, 3H, J=7.5 HZ), 0.97 (d, 3H, J=6 Hz), 0.19 (s, 9H); $^{13}$C NMR (100 MHz, CDCl$_3$), δ: 166.2, 159.5, 159.1, 157.1, 131.0, 130.6, 128.8, 114.3, 111.0, 80.5, 79.2, 75.9, 57.1, 55.5, 50.9, 31.8, 27.9, 19.0, 17.5, −1.3; HRMS (ES+) calcd for C$_{26}$H$_{43}$N$_2$O$_6$Si [MH]$^+$ 531.2890. Found 531.2895.

* See, Ishizuka, T.; Kunieda, T. Tetrahedron Lett. 1987, 28, 4185-4188.

EXAMPLE 7

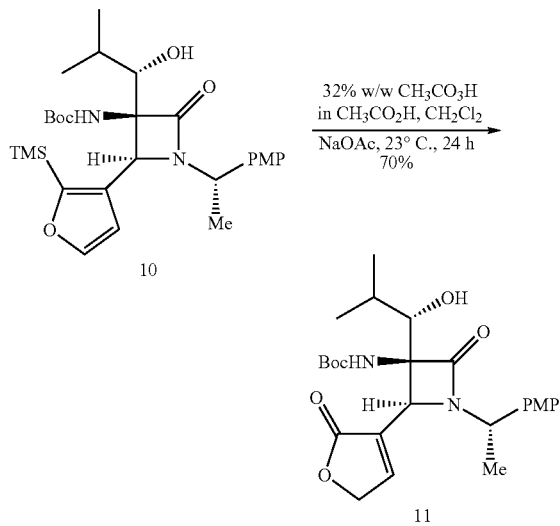

Butenolide—Compound 11. To a solution of the 2-trimethylsilylfuran (Compound 10) (951 mg, 1.79 mmol, 1 equiv) in dichloromethane (12 mL) was added sodium acetate (830 mg, 10.1 mmol, 5.7 equiv) and peroxyacetic acid (2 mL, 32% w/w in acetic acid).* The resultant biphasic mixture stirred for 18 h at 23° C. at which time an additional portion of peroxyacetic acid solution (500 µL) was added. After 6 h the reaction was partitioned between dichloro-methane (200 mL) and saturated aqueous sodium sulfite solution (50 mL). The organics were dried over sodium sulfate and concentrated in vacuo. The residue was purified by flash chromatography on silica gel (gradient elution 10-25-50% ethyl acetate in dichloro-methane) to give the butenolide, Compound 11 (591 mg, 1.25 mmol, 70%) as a colorless solid, mp 213-215° C. (dc). $R_f$=0.34 (70% ethyl acetate in hexanes). $[\alpha]^{23}{}_D$+34.35 (c 0.69, CHCl$_3$); FTIR (neat), cm$^{-1}$: 3263, 2983, 1750, 1684; $^1$H NMR (500 MHz, CDCl$_3$), δ: 7.32 (d, 1H, J=1 Hz), 7.23 (d, 2H, J=9 Hz), 6.87 (d, 2H, J=9 Hz), 5.30 (s, 1H), 5.03 (q, 1H, J=7 Hz), 4.76 (ABQ, 2H, J=18.5 Hz), 4.31 (bs, 1H), 3.81 (s, 3H), 3.59 (bs, 1H), 3.40 (t, 1H, J=5 Hz), 2.03 (m, 1H), 1.59 (d, 3H, J=6.5 Hz), 1.34 (s, 9H), 0.99 (d, 3H, J=7 Hz), 0.97 (d, 3H, J=6.5 Hz); $^{13}$C NMR (100 MHz, CDCl$_3$), δ: 173.5, 165.7, 159.6, 155.3, 150.0, 132.0, 129.5, 128.5, 114.4, 80.7, 78.2, 76.3, 71.2, 59.4, 55.5 52.4, 30.7, 28.2, 21.2, 19.2, 17.4; HRMS (ES+) Calcd for C$_{25}$H$_{35}$N$_2$O$_7$ [MH]+ 475.2444. Found 475.2453.

* See, Isao, K.; Urabe, H. Tetrahedron Lett. 1981, 22, 5191-5194.

EXAMPLE 8

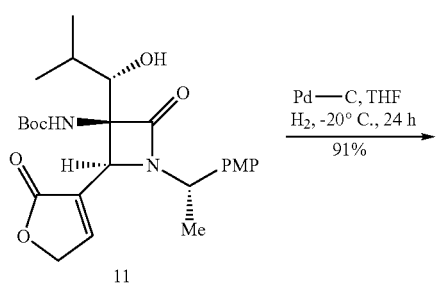

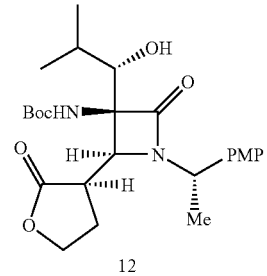

Butyrolactone—Compound 12. To a solution of the butenolide, Compound 11 (360 mg, 0.76 mmol, 1 equiv) in THF (35 mL) at −20° C., was added 10% Pd on carbon (350 mg). The resultant suspension was placed under a balloon atmosphere of hydrogen and stirred for 24 h. The resultant mixture was filtered through Celite and the filtrate was concentrated in vacuo. The resultant residue was purified by flash chromatography on silica gel (gradient elution 40-50-60-75% ethyl acetate in hexanes) to provide Compound 12 (328 mg, 0.69 mmol, 91%) as a colorless solid, mp 148-150° C. $R_f$=0.29 (60% ethyl acetate in hexanes). $[\alpha]^{23}{}_D$−24.6 (c 0.52, CHCl$_3$); FTIR (neat), cm$^{-1}$: 3425, 2977, 1752, 1733, 1717, 1515, 1490, 1165, 729; $^1$H NMR (500 MHz, CDCl$_3$), δ: 7.29 (d, 2H, J=8.5 Hz), 6.88 (d, 2H, J=9 Hz), 5.45 (s, 1H), 4.98 (q, 1H, J=7 Hz), 4.25 (dt, 1H, J=1.5, 9 Hz), 4.17(m, 1H), 3.81 (d, 1H, obscured by OCH$_3$ signal), 3.81 (s, 3H), 3.68 (bs, 1H), 3.43 (t, 1H, J=5.5 Hz), 2.85 (dt, 1H, J=6, 11 Hz), 2.39 (m, 1H), 2.16 (m, 2H), 1.61 (d, 3H, J=7.5 Hz), 1.41 (s, 9H), 1.01 (d, 3H, J=7 Hz), 0.98 (d, 3H, J=6.5 Hz); $^{13}$C NMR (100 MHz, CDCl$_3$), δ: 178.1, 165.6, 159.4, 155.5, 132.15, 128.6, 114.3, 81.1, 79.0, 73.9, 67.3, 63.3, 55.5, 52.7, 39.8, 30.5, 28.1, 25.1, 21.5, 19.3, 17.1; HRMS (ES+) Calcd for C$_{25}$H$_{37}$N$_2$O$_7$ [MH]$^+$ 477.2601. Found 475.2592.

EXAMPLE 9

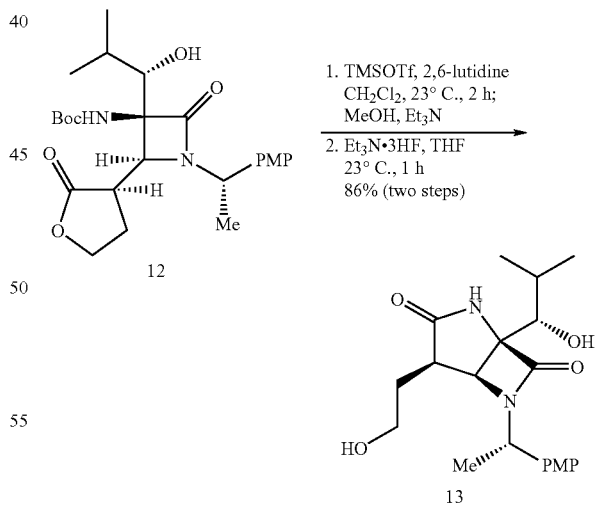

Butyrolactam—Compound 13. To a solution of the butyrolactone, Compound 12 (100 mg, 0.21 mmol, 1 equiv) in dichloromethane (4 mL) at 23° C. was added 2,6-lutidine (195 µL, 1.68 mmol, 8 equiv) followed by trimethylsilyl trifluoromethanesulfonate (150 µL, 0.84 mmol, 4 equiv). After 2 h, triethylamine (500 µL) was added to the reaction followed by methanol (500 µL). The solution was concentrated in vacuo. To the resultant residue was added THF (3 mL) and triethylamine trihydrofluoride (400 μL). The mixture was stirred for 1 h at 23° C. at which time the reaction was partitioned between ethyl acetate (100 mL) and aqueous hydrochloric acid (2N, 20 mL). The organics were further washed with saturated aqueous sodium bicarbonate (20 mL) and saturated aqueous sodium chloride (20 mL). The organics were dried over sodium sulfate and concentrated in vacuo. The resultant residue was purified by flash chromatography on silica gel (gradient elution 2-4-6-8-10% methanol in dichloromethane) to give Compound 13 (67 mg, 0.179 mmol, 85%) as a colorless solid, mp 166-168° C. $R_f$=0.36 (10% methanol in dichloromethane). $[\alpha]^{23}_D$+25.6 (c 0.62, CHCl$_3$); FTIR (neat), cm$^{-1}$: 3381, 3296, 2964, 2935, 1737, 1683, 1515, 1246, 1507; $^1$H NMR (600 MHz, CD$_3$OD), δ: 7.34 (d, 2H, J=8.5 Hz), 6.89 (d, 2H, J=9 Hz), 4.56 (q, 1H, J=6.5 Hz), 3.85 (d, 1H, J=4 Hz), 3.78 (s, 3H), 3.62 (t, 1H, J=6 Hz), 2.64 (m, 1H), 1.84 (m, 1H), 1.68 (m, 1H), 1.67 (d, 3H, J=7 Hz), 1.48 (m, 1H), 1.04 (d, 3H, J=7 Hz), 0.91 (d, 3H, J=6.5 Hz); $^{13}$C NMR (100 MHz, CD$_3$OD), δ: 178.4, 172.2, 159.2, 134.3, 128.1, 113.8, 75.3, 71.5, 60.3, 59.2, 56.5, 54.5, 41.9, 29.6, 28.8, 20.6, 19.5, 16.0; HRMS (ES+) Calcd for C$_{20}$H$_{29}$N$_2$O$_5$ [MH]$^+$ 377.2076. Found 377.2076.

EXAMPLE 10

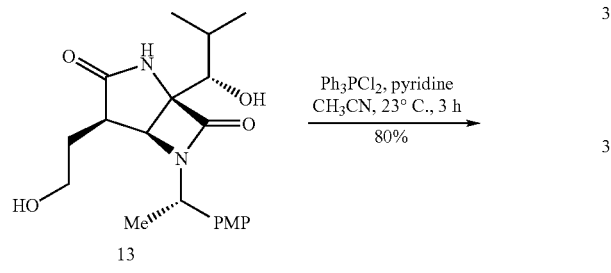

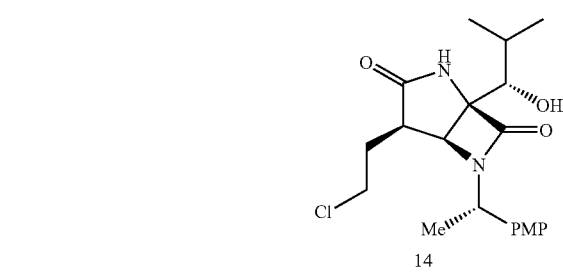

Chloride—Compound 14. To a solution of the alcohol 13 (181 mg, 0.481 mmol, 1 equiv) in acetonitrile (4 mL) was added pyridine (90 μL, 1.44 mmol, 3 equiv) and dichlorotriphenylphosphorane (240 mg, 0.72 mmol, 1.5 equiv). The resultant solution was allowed to stir 4 h at 23° C., and was then partitioned between ethyl acetate (200 mL) and saturated aqueous sodium bicarbonate (βΣ 25 mL). The organics were further washed with aqueous hydrochloric acid (2N, 50 mL) and saturated aqueous sodium chloride (25 mL). The organics were dried over sodium sulfate and concentrated in vacuo. The resultant residue was purified by flash chromatography on silica gel (gradient elution 25-50-100% ethyl acetate in hexanes) to provide Compound 14 (148 mg, 0.57 mmol, 80%) as a colorless solid, mp 206° C. $R_f$=0.5 (10% methanol in dichloromethane). $[\alpha]^{23}_D$+19.1 (c 0.54, CHCl$_3$; FTIR (neat), cm$^{-1}$: 3336, 2968, 1735, 1710, 1248; $^1$H NMR (500 MHz, CDCl$_3$), δ: 7.54 (s, 1H), 7.27 (d, 2H, J=9 Hz), 6.84 (d, 2H, J=9 Hz), 4.54 (d, 1H, J=7 Hz), 4.45 (q, 1H, J=7 Hz), 3.89 (m, 1H), 3.77 (s, 3H), 3.67 (m, 1H), 3.62 (m, 1H), 3.57 (d, 1H, J=7 Hz), 2.63 (q, 1H, J=7 Hz), 2.03 (m, 1H), 1.89 (m, 1H), 1.68 (m, 1H), 1.64 (d, 3H, J=7 Hz), 1.02 (d, 3H, J=6.5 Hz), 0.90 (d, 3H, J=6]Hz); $^{13}$C NMR (100 MHz, CD$_3$OD), δ: 178.4, 172.2, 159.2, 134.3, 128.1, 113.8, 75.3, 71.5, 60.3, 59.2, 56.5, 54.5, 41.9, 29.6, 28.8, 20.6, 19.5, 16.0; HRMS (ES+) Calcd for C$_{20}$H$_{28}$ClN$_2$O$_4$ [MH]$^+$ 395.1738. Found 395.1744.

EXAMPLE 11

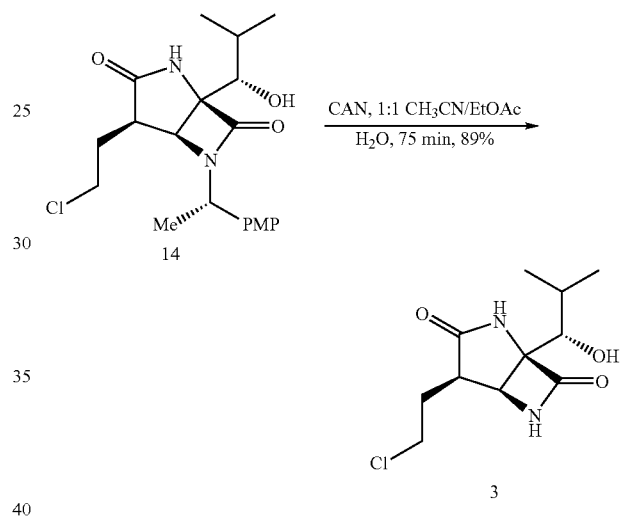

β-lactam—Compound 3. To a solution of the α-methylbenzyl amide, Compound 14 (148 mg, 0.57 mmol, 1 equiv) in 1:1 acetonitrile/ethyl acetate (8 mL) was added water (2 mL) followed by ammonium cerium (IV) nitrate (823 mg, 2.28 mmol, 4 equiv). The resultant mixture was allowed to stir for 75 min at 23° C. The reaction was partitioned between ethyl acetate (200 mL) and saturated aqueous sodium bicarbonate (25 mL). The organics were further washed with saturated aqueous sodium chloride (25 mL). The organics were dried over sodium sulfate and concentrated in vacuo. The resultant residue was purified by flash chromatography on silica gel (10% methanol in dichloromethane) to give Compound 3 (87 mg, 0.51 mmol, 89%) as a colorless solid, mp 205-207° C. $R_f$=0.34 (10% methanol in dichloromethane). $[\alpha]^{23}_D$−83.8 (c 0.50, CH$_3$OH); FTIR (neat), cm$^{-1}$: 3244, 2966, 1756, 1690; $^1$H NMR (500 MHz, CDCl$_3$), δ: 4.45 (d, 1H, J=6.5 Hz), 3.85-3.79 (m, 2H), 3.74 (m, 1H), 2.77 (m, 1H), 2.26 (m, 1H), 2.00(m, 1H), 1.86 (m, 1H), 1.05 (d, 3H, J=7 Hz), 0.92 (d, 3H, J=7 Hz); $^{13}$C NMR (100 MHz, CD$_3$OD), δ: 177.9, 171.7, 78.3, 71.4, 52.9, 42.9, 41.6, 29.7, 28.6, 19.3, 16.0; HRMS (ES+) Calcd for C$_{11}$H$_{18}$N$_2$O$_3$ [MH]$^+$ 261.1006. Found 261.1009.

EXAMPLE 12

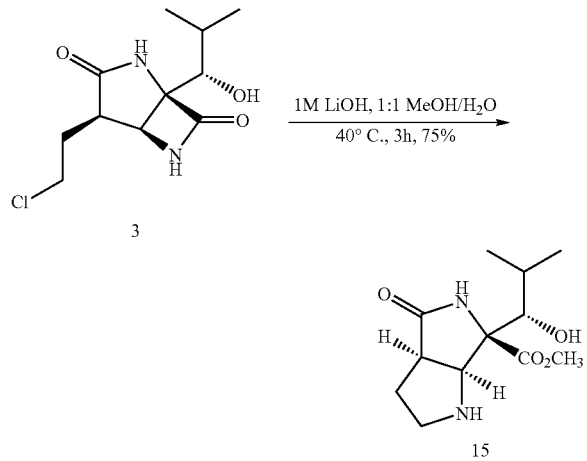

Pyrollidine—Compound 15. To a solution of the β-lactam 3 (10.6 mg, 41 μmol, 1 equiv) in methanol (0.5 mL) and water (0.5 mL) was added lithium hydroxide (1 mmol, 24.6 equiv) and the resultant suspension was warmed to 40° C. After consumption of starting material was observed (3 h), the reaction was partitioned between ethyl acetate (20 mL) and saturated aqueous sodium chloride (20 mL). The organics were dried over sodium sulfate and concentrated in vacuo. The resultant residue was purified by flash chromatography on silica gel (10% methanol in dichloromethane) to provide Compound 15 (7.8 mg, 30 μmol, 75%) as a colorless solid. $R_f$=0.34 (10% methanol in dichloromethane). FTIR (neat), cm$^{-1}$: 3224, 1735, 1679, 1262; $^1$H NMR (500 MHz, CD$_3$OD), δ: 3.94 (d, 1H, J=6.5 Hz), 3.77 (d, 1H, J=7.5 Hz), 3.74 (s, 3H), 3.10 (m, 1H), 2.82 (m, 1H), 2.67(m, 1H), 1.96 (m, 1H), 1.87 (m, 1H), 1.65 (m, 1H), 0.99 (d, 3H, J=7 Hz), 0.84 (d, 3H, J=7 Hz); HRMS (ES+) Calcd for $C_{12}H_{21}N_2O_4$ [MH]$^+$ 257.1501. Found 257.1497.

EXAMPLE 13

Inactivation of 20S proteasome by Compound 3. To separate 50 mL vials containing 12 mL of pH 7.9 buffer (20 mM hepes, 0.5 mM EDTA) was added 60 μL of a stock solution of 20S proteasome (20 mM Hepes, 0.5 mM EDTA, pH 7.9, 100 μg/mL) and aqueous sodium dodecylsulfate (10% w/v, 30 μL). The initial rate of hydrolysis of Suc-Leu-Leu-Val-TyrAMC was determined by addition of a solution of Suc-Leu-Leu-Val-Tyr-AMC (10 mM in DMSO, 10 μL) to a 2 mL aliquot of each of the above solutions. The initial rate of free AMC production was monitored at 37° C. by fluorescence spectrophotometry as described by Dick et al.* To one of the stock solutions was added a solution of the β-lactam 3 (10 mM in DMSO, 12 μL). Both solutions were incubated side by side at 37° C. Aliquots were removed at time points as assayed as above. The data for both the 10 μM experiment and an identical experiment utilizing 30 μM using a 30 mM stock solution of 3 are tabulated below.

* See, McCormack, T.; Baumeister, W.; Grenier, L.; Moomaw, C.; Plamondon, L.; Pramanik, B.; Slaughter, C.; Soucy, F.; Stein, R.; Zuhl, F.; Dick, L., J. Biol. Chem. 1996, 272, 26103-26109.

Time Course Measurements

| Time | Control (units F/s) | % Initial velocity | Experiment with 10 μM 3 units F/s | % Initial Velocity |
|---|---|---|---|---|
| Part 1-10 μM of Compound 3 | | | | |
| 0 h | 0.696 | 100 | 0.59 | 100 |
| 1.5 h | 0.575 | 83 | 0.337 | 57 |
| 2.5 h | 0.600 | 86 | 0.267 | 45 |
| 4.5 h | 0.527 | 76 | 0.156 | 26 |
| 6.5 h | 0.52 | 74 | 0.09 | 15 |
| 9.5 h | 0.337 | 48 | 0.044 | 7.4 |
| Part 2-30 μM of Compound 3 | | | | |
| 0 mm | 0.566 | 100 | 0.526 | 100 |
| 47 mm | 0.480 | 85 | .233 | 44 |
| 101 mm | 0.394 | 70 | 0.090 | 17 |
| 177 mm | 0.390 | 69 | 0.039 | 7 |

REFERENCES

The following references are cited herein as background information:

(1) Feling, A. H.; Buchanan, G. O.; Mincer, T. J.; Kauffman, C. A.; Jensen, P. A.; Fenical, W., Angew. Chem. Int. Ed. 2003, 42, 355-357.

(2) (a) Reviewed in: Corey, E. J., Li, W. -D. Z., Chem. Pharm. Bull. 1999, 47, 1-10. (b) Corey, E. J.; Reichard, G. A.; Kania, A., Tetrahedron Lett. 1993, 34, 6977-6980. (c) Corey, E. I.; Reichard, G. A., J. Am. Chem. Soc. 1992, 114, 10677-10678. (d) Fenteany, G.; Standaert, R. F.; Reichard, G. A.; Corey, E. J.; Schreiber, S. L., Proc. Nat'l. Acad. Sci. USA 1994, 91, 3358-3362.

(3) (a) Omura, S.; Fujimoto, T.; Otoguro, K.; Matsuzaki, K.; Moriguchi, R.; Tanaka H.; Sasaki, Y., J. Antibiot. 1991, 44, 113-116. (b) Omura, S.; Matsuzaki, K.; Fujimoto, T.; Kosuge, K.; Furuya, T.; Fujita, S.; Nakagawa, A., J. Antibiot. 1991, 44, 117-118.

(4) Bortezomib (Velcade®-Millennium)—a peptidyl boronic acid which is a reversible (0.6 nM K) proteasome inhibitor is currently in use and approved for the treatment of multiple myeloma. In addition, there are numerous ongoing clinical trials on the use of this agent for treatment of other malignant diseases. See: (a) Richardson, P. G.; Hideshima, T.; Anderson, K. C., Cancer Control 2003, 10, 361-369. (b) Steinberg, D., The Scientist 2003, 17(52), S18-S22. (c) Adams, J., Proteasome Inhibitors in Cancer Therapy, Human Press, New York, 2004.

(5) Reddy, L. A.; Saravanan, P.; Corey, E. J., J. Am. Chem. Soc. 2004, 126, 6230-6231. (b) Reddy, L. R.; Fournier, J. F., Reddy, B. V. S, Corey, E. J., J. Am. Chem. Soc. 2005, 127, 8974-8976. (c) Endo, A.; Danishefsky, S. J., J. Am. Chem. Soc. 2005, 127, 8298-8299.

(6) Xiang, C.; Wang, W.; Hruby, V. J., J. Org. Chem. 2002, 67, 35143517.

(7) Ghosez, L.; George-Koch, I.; Pating, L.; Houtekie, M.; Bovy, P.; Nshimyumuzika, P. Phan, T., Tetrahedron 1998, 54, 9207-9222.

(8) See the Examples.

(9) Ishizuka, T.; Kunieda, T., Tetrahedron Lett. 1987, 28, 4185-4188.

(10) Isao, K.; Urabe, H., Tetrahedron Lett. 1981, 22, 5191-5194.

(11) McCormack, T.; Baumeister, W.; Grenier, L.; Moomaw, C.; Plamondon, L.; Pramanik, B.; Slaughter, C.; Soucy, F.; Stein, R.; Zuhl, F.; Dick, L., J. Biol. Chem. 1997, 272, 26103-26109.

(12) Obtained from Boston Biochem.

(13) In vitro proteasome preparations are much less stable than the native in vivo proteins.

The present invention has been described in detail, including the preferred embodiments thereof. However, it will be appreciated that those skilled in the art, upon consideration of the present disclosure, may make modifications and/or improvements on this invention and still be within the scope of this invention as set forth in the following claims.

What is claimed is:

1. Compound 3, having the formula:

3 and pharmaceutically acceptable salts thereof.

2. A method for the synthetic formation of Compound 3:

3 comprising the steps of:

(a) reacting Compound 4 with phenyl chloroformate in dichloromethane, followed by reduction of the azido group and intramolecular cyclization to form the oxazolidinone, Compound 5:

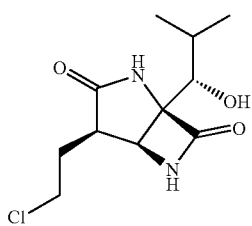

(b) N-protection of Compound 5 to generate Compound 6:

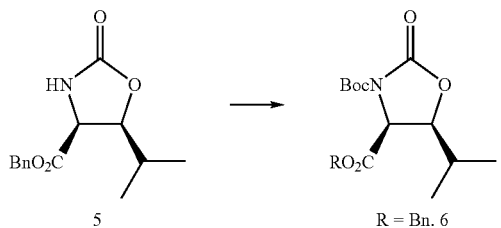

(c) cleavage of the benzyl ester subunit in Compound 6 to provide the carboxylic acid Compound 7:

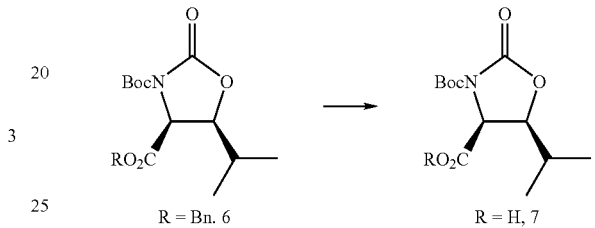

(d) reaction of Compound 7 with Compound 8 to form the β-lactam, Compound 9:

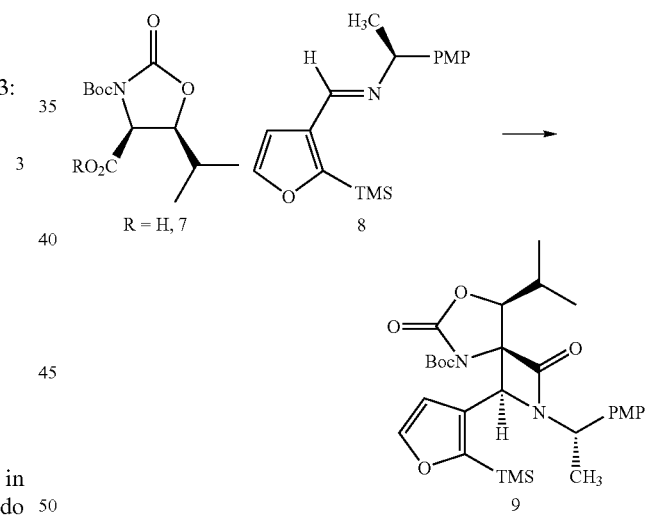

(e) cleavage of the oxazolidinone ring in Compound 9 to afford the alcohol 10:

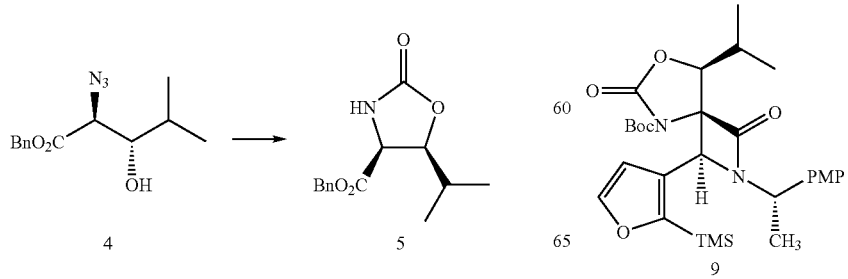

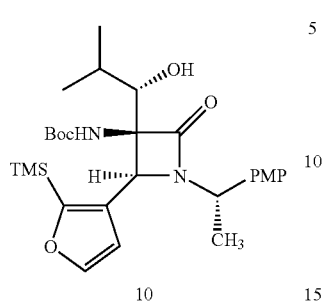

(f) oxidation of the 2-trimethsilylfuran subunit in Compound 10 to give the butenolide, Compound 11:

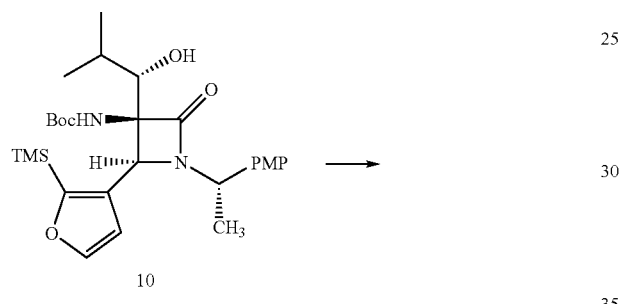

(g) catalytic reduction of Compound 11 to provide the butyrolactone, Compound 12:

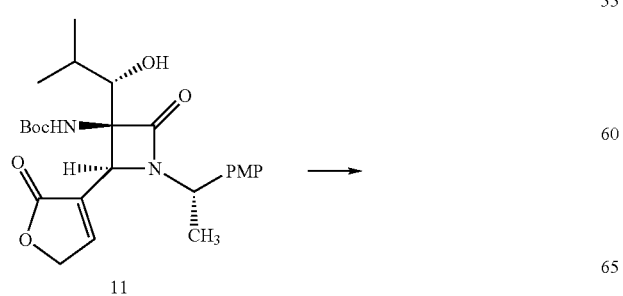

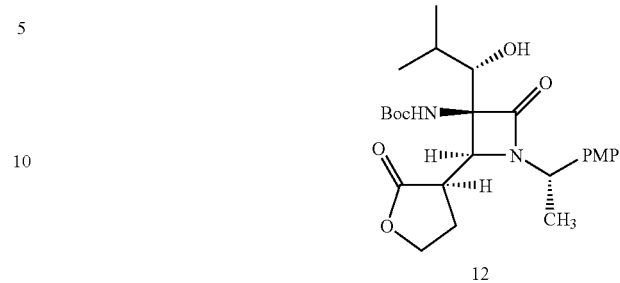

(h) cleavage of the t-butoxycarboxyl group of Compound 12 followed by fluoride treatment to provide the butyrolactam, Compound 13:

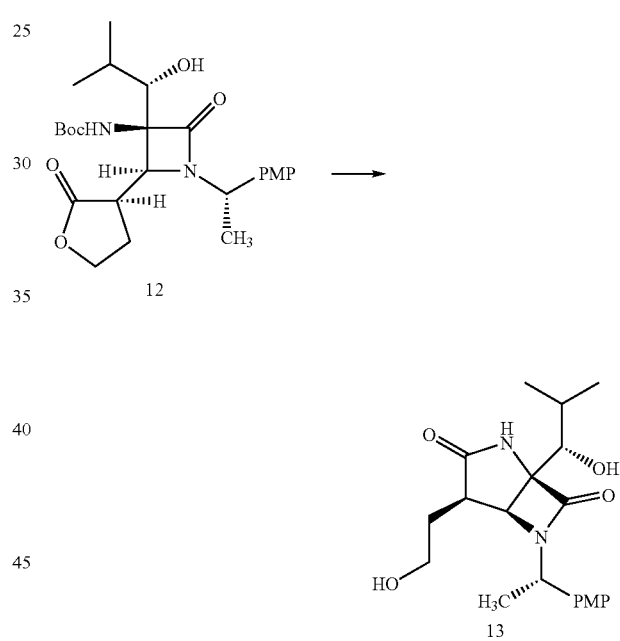

(i) changing the primary hydroxyl atom of Compound 13 to chlorine, to give Compound 14:

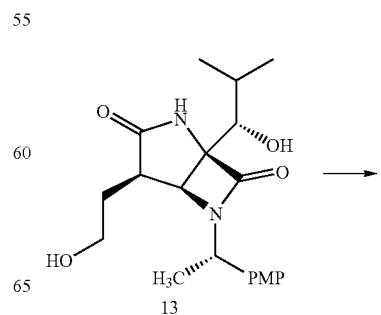

-continued

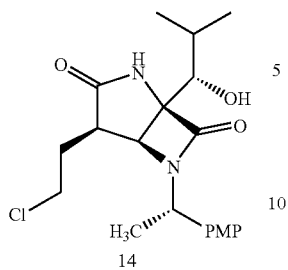

14 and (j) oxidative cleavage of the (S)(−)-(4-methoxyphenyl)-ethylamide protecting group in Compound 14 to give the β-lactam, Compound 3:

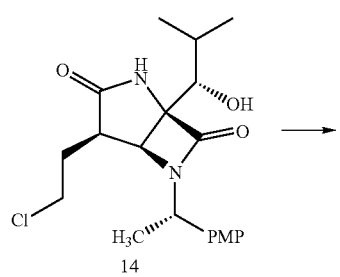

14

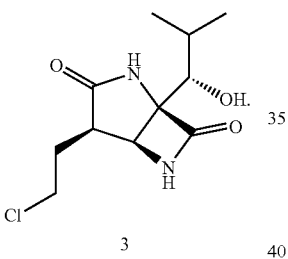

3

3. The method of claim 2, further including the step of forming Compound 8, by reacting Compound A with Compound B:

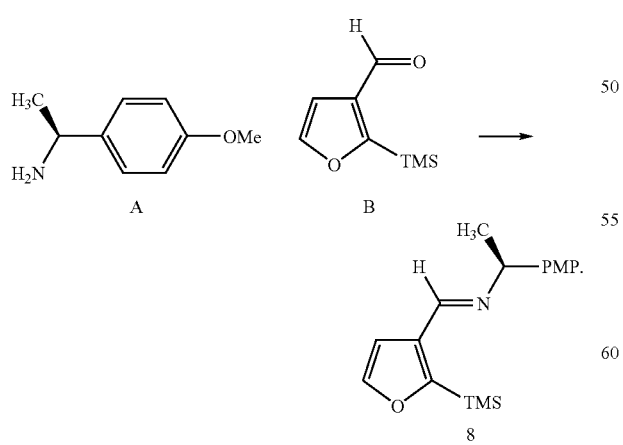

4. A pharmaceutical composition comprising a compound of formula 3,

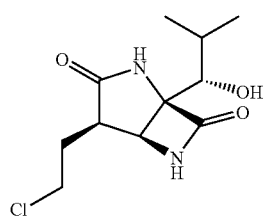

and a pharmaceutically acceptable carrier or diluent.

5. A pharmaceutical composition comprising a compound of formula 14,

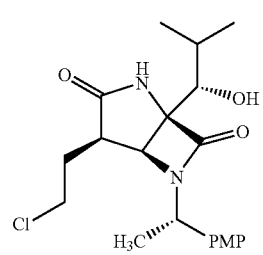

14 and a pharmaceutically acceptable carrier or diluent.

6. A pharmaceutical composition comprising a compound of formula 13,

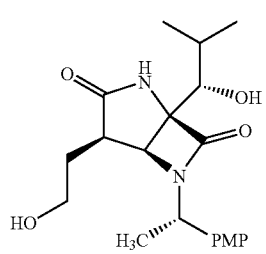

13 and a pharmaceutically acceptable carrier or diluent.

7. A pharmaceutical composition comprising a compound of formula 12,

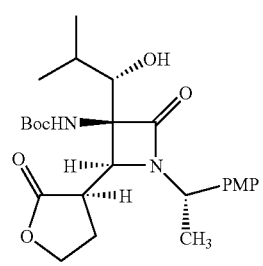

12 and a pharmaceutically acceptable carrier or diluent.

8. A pharmaceutical composition comprising a compound of formula 11,

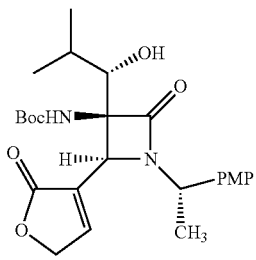

and a pharmaceutically acceptable carrier or diluent.

9. A pharmaceutical composition comprising a compound of formula 10,

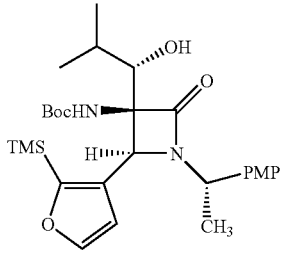

and a pharmaceutically acceptable carrier or diluent.

10. A pharmaceutical composition comprising a compound of formula 9,

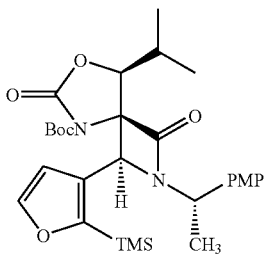

and a pharmaceutically acceptable carrier or diluent.

11. A method of inhibiting proteasome proteolytic activity in a cell, comprising said cell with Compound 3:

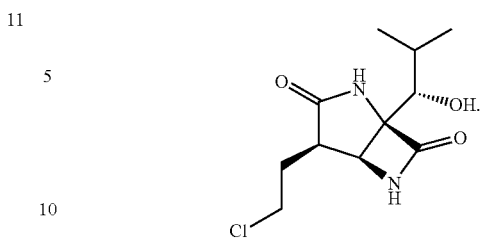

12. A method of inhibiting proteasome proteolytic activity in a mammal, comprising administering to said mammal Compound 3:

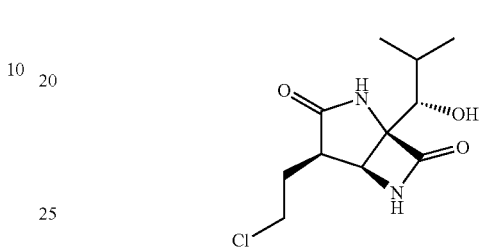

in an amount effective to inhibit proteasome proteolytic activity.

13. A method of treating ischemic or reperfusion injury in a mammal comprising administering to said mammal an effective amount of Compound 3:

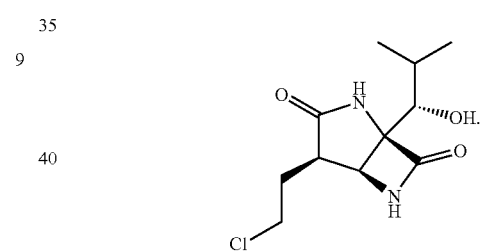

14. The method of claim 13, wherein the ischemia is the result of vascular occlusion.

15. The method of claim 13, wherein said vascular occlusion occurs during a stroke.

* * * * *